US006472183B2

United States Patent
Prideaux et al.

(10) Patent No.: US 6,472,183 B2
(45) Date of Patent: Oct. 29, 2002

(54) **IMMUNITY AGAINST *ACTINOBACILLUS PLEUROPNEUMONIAE*'S RTX TOXINS APX**

(75) Inventors: Christopher Thomas Prideaux, Coburg North (AU); Adrian Leslie Mark Hodgson, Newtown (AU)

(73) Assignees: Commonwealth Scientific and Industrial Research Organisation, Campbell (AU); Pig Research and Development Corporation, Barton (AU)

(*) Notice: Subject to any disclaimer, the term of this patent is extended or adjusted under 35 U.S.C. 154(b) by 0 days.

(21) Appl. No.: 09/068,086

(22) PCT Filed: Nov. 1, 1996

(86) PCT No.: PCT/AU96/00686

§ 371 (c)(1),
(2), (4) Date: Jun. 19, 1998

(87) PCT Pub. No.: WO97/16532

PCT Pub. Date: May 9, 1997

(65) Prior Publication Data

US 2002/0022035 A1 Feb. 21, 2002

(30) Foreign Application Priority Data

Nov. 2, 1995 (AU) .............................. PN 6314

(51) Int. Cl.[7] .............................................. C12P 21/04
(52) U.S. Cl. ................ 435/71.1; 435/320.1; 435/172.1; 435/172.3; 435/243; 435/252.3; 435/252.8; 435/69.1; 435/69.3; 435/69.7; 536/23.1; 536/23.7; 424/184.1; 424/234.1; 424/236.1; 424/235.1
(58) Field of Search .......................... 424/184.1, 234.1, 424/236.1, 235.1; 536/23.1, 23.7; 435/320.1, 172.1, 172.3, 243, 252.3, 252.8, 69.1, 69.3, 69.7, 71.2

(56) References Cited

U.S. PATENT DOCUMENTS 6,180,112 B1 * 1/2001 Highlander et al.

FOREIGN PATENT DOCUMENTS

| CA | 2170839 | 9/1996 |
| EP | 0549066 | 6/1993 |
| EP | 0810283 A2 | 12/1997 |
| WO | 9106653 | * 5/1991 |

OTHER PUBLICATIONS

Molecular Microbiology 14(2), 1994, pp. 207–216, Tacson et al, "The RTX haemolysins APXI and APXII are major virulence . . . ".

Infection and Immunity, vol. 63, No. 1, (Jan. 1995), pp. 27–37, Jansen et al, "Knockout Mutants of Actinobacillus . . . ".

Veterinary Microbiology, 29, (1991), pp. 146–158, Bhatia et al, "Factors involved in immunity against Actinobacillus . . . ".

Infection and Immunity, vol. 61, No. 10, (Oct. 1993), pp. 4462–4468, Michalski et al, "CVD110, an Attenuated Vibrio . . . ".

Microbial Pathogenesis, (1995), pp. 197–209, Reiner et al, "Molecular investigation of the role of APXI and APXII in . . . ".

Molecular Microbiology, 4(11), (1990), pp. 1933–1939, Cruz et al, "Deletion analysis resolves cell–binding and lytic . . . ".

Microbial Pathogenesis, 18, (1995), pp. 307–321, Guthmiller et al, "Mutational analsyis of the putative leukotoxin transport . . . ".

Infection and Immunity, vol. 63, No. 3, (Mar. 1995), pp. 1027–1032, Chidambaram et al, "Isolation of Pasteurella . . . ".

Infection and Immunity, 59, (1991), pp. 4110–4116, Anderson et al, "Isolation and molecular characterization of . . . ".

Vet. Microb. 28, (1991), pp. 147–158, Bhatia et al, "Factors involved in the immunity against Actinobacillus . . . ".

FEMS Micro. Rev. 88, (1992), pp. 137–162, Coote, "Structural relationships among the RTX determinants of Gram–negative . . . ".

Infect. Immun. 58, (1990), pp. 358–365, Fedorka, Cray et al, "Efficacy of cell extract from Actinobacillus . . . ".

J. Bacte. 163, (1985), pp. 88–93, Felmelle et al, "*Escherichia coli* hemolysin is released extracellularly without cleavage . . . ".

Infect. Immun. 54, (1986), pp. 575–582, Fenwick et al, "Immune responses to the Lipopolysaccharides and capsular . . . ".

Infection and Immunity 26, (1988), pp. 2570–2575, "Recognition of Hemolysin expression in *Actinobacillus pleuropneumoniae* . . . ".

J. Clin. Microbiol. 28, (1990), pp. 232–236, Frey et al, Hemolysin patterns of *Actinobacillus pleuropneumoniae*.

Infect. Immun. 59, (1991), pp. 3026–3032, "Nucleotide sequence of the hemolysin I gene from Actinobacillus pleuropneumoniae".

Infect. Immun. 60, (1992), Frey et al, "Identification of a second hemolysis (hlyII) in Actinobacillus. . . ", pp. 1671–1676.

(List continued on next page.)

*Primary Examiner*—Jennifer E. Graser
(74) *Attorney, Agent, or Firm*—Jacobson Holman, PLLC

(57) ABSTRACT

Disclosed herein is a modified microorganism which produces an RTX toxin, wherein said RTX toxin is partially or fully inactivated. Also disclosed is a modified microorganism wherein an RTX toxin gene including an RTX structural gene and/or a post-translational activator of the organism is partially or full inactivated. As disclosed, the precursor of an RTX toxin has reduced toxic activity.

15 Claims, 12 Drawing Sheets

OTHER PUBLICATIONS

Gene 123, (1993), Frey et al, Analysis of hemolysin operons in Actinobacillus pleuropneumoniae, pp. 51–58.

J. Gen. Micro. 139, (1993), pp. 1723–1728, Frey et al, "*Actinobacillus pleuropneumoniae* RTX–toxins: uniform designation . . . ".

Microb. Pathogen 10, (1991), pp. 281–296, Inzana et al, "Characterization of a non–hemolytic mutant of . . . ".

Nature, 351, (1991), pp. 759–761, Issartel et al, "activation of *Escherichia coli* prohaemolysin to the mature toxin by . . . ".

Infect. Immun. 59, (1991), pp. 3079–3085, Kamp et al, "Identification of hemoloytic and cytotoxic proteins of . . . ".

Vet. Microbiol. 25, (1990), pp. 229–240, "Grouping of *Actinobacillus pleuropneumoniae* strains of serotypes 1 through 12 . . . ".

Nature, 227, (1970), pp. 680–685, Laemmli, "Cleavage of structural proteins during the assembly of the head of . . . ".

Vet. Microbiol. 18, (1988), pp. 335–348, Lenser et al, "Protection of mice against lethal effects of an . . . ".

Gene 32, (1984), pp. 482–485, Marsh et al, "The plC plasmid and phage vectors with versatile cloning sites for recombinant . . . ".

J. Immunol. Methods 135, (1990), pp. 277–280, McKimm–Breschkin, "The use of teramethylbenzidine for solid phase immunoassays".

Proc. 10$^{th}$ Int. Pig Veterinary Society Congress, (1988), p. 81 Mulks et al, "Efficacy of *Actinobacillus pleuropneumoniae* . . . ".

Gene, 148, (1994), pp. 101–105, Murphy et al, "Construction of isogenic mutants of Pasteurella Hamolytic by allelic. . . ".

Int. J. Syst. Bacteriol 33, (1983), pp. 510–514, Pohl etal, "Transfer of *Heaemophilus pleuropneumoniae* and the . . . ".

Infect. Immun. 54, (1986), pp. 751–760, Rapp et al, "Antibody response of swine to outer membrane components of . . . ".

Am. J. Vet. Res. 51, (1990), pp. 711–717, Rosendale et al, "Characterization of an attenuated wtrain of Actinobacillus . . . ".

Am. J. Vet. Res. 49, (1988), pp. 1053–1058, Rosendale et al, "Evanluation of heat–sensitive, neutrophil–toxic, and . . .".

J. Gen. Microbiol. 137, (1991), pp. 561–568, Rycroft et al, "The cytotoxin of *Actinobacillus pleuropneumoiae* . . . ".

Vet. Rec. 16, (1991), pp. 441–443, Rycroft et al, "Experimental reproduction of actue lesions of porcine pleuropneumoniae. . . ".

J. Bacteriol 175, (1993), Tascon et al, "Transposon mutagenesis in *Actinobacillus pleuropneumoniae* with TnIO derivative".

Mol. Micro. 14, (1994), pp. 207–216, Tascon et al, "The RTX Haemolysisns ApxI and ApxII are major virulence factors of . . . ".

Arn. J. Vet. Res. 48, (1987), pp. 768–773, Udeze et al, "Role of *Haemophilu pleuropneumoniae* lipopolysaccharide endotoxin . . . ".

Mol. Microbiol. 5, (1991), pp. 521–528, Welch, "Pore–forming cytolysins of Gram–negative bacteria".

Gene 33, (1985), Yanisch–Perron et al, pp. 103–119, "Improved M13 phage cloning vectors and host strains: nucleotide . . . ".

Medline Abstract 2307519, C. Forestier et al, Infect. Immun., 58(3), pp. 828–832, 1990.

Medline Abstract 1419113, C. Hughes et al, FEMS Microbiol. Immunol. 5(1–3), pp. 37–43, 1992.

Jansen et al, Infection and Immunity, vol. 61, No. 9, "Structural Analysis of . . . ", pp. 3688–3695, Sep. 1993.

Frey, Trends in Microbiology, vol. 3, No. 7, "Virulence in Actinobacillus . . . ", pp. 257–261, Jul. 1995.

Van Den Bosch et al, Third Intl. Conf. On Haemophilus . . . , "An *Actinobacillus Pleuropneumoniae* . . . ", abstract, 1994.

Prideaux et al, Third Intl. Conf. On Haemophilus. . . , Development of Actinobacillus. . . , abstract, 1994.

Michel et al, Molecular Microbiology, vol. 4, No. 12, "Attenuated Mutants of the . . . ", pp. 2167–2178, 1990.

* cited by examiner

FIG. 1
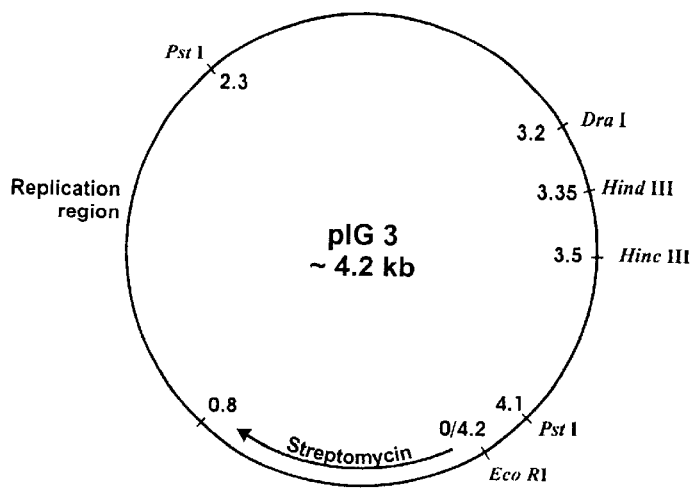
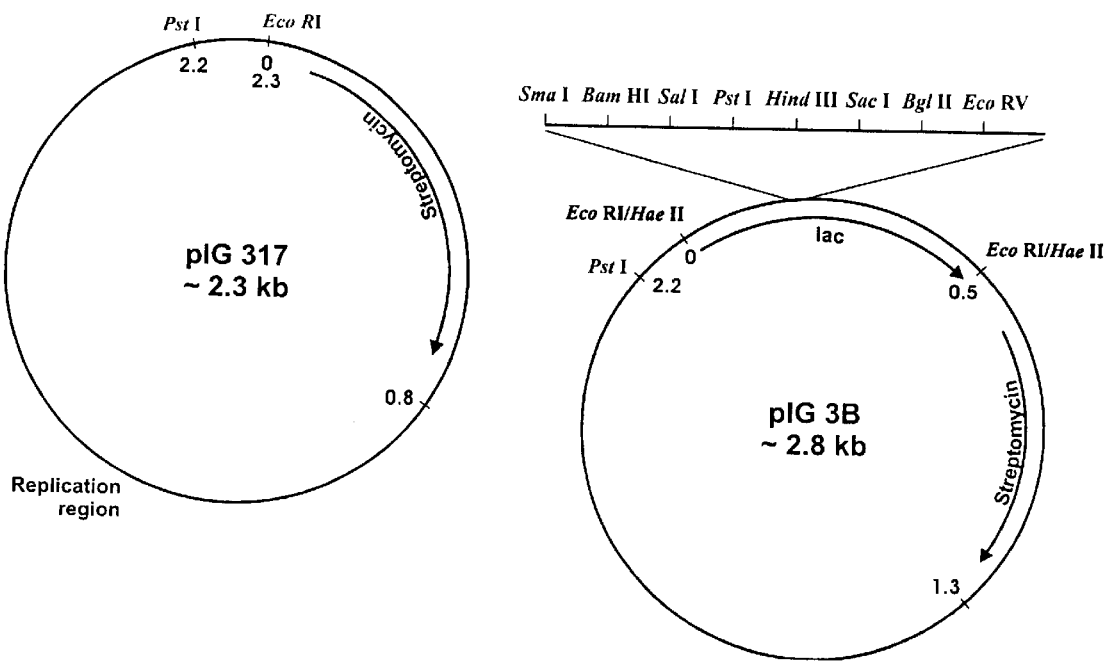

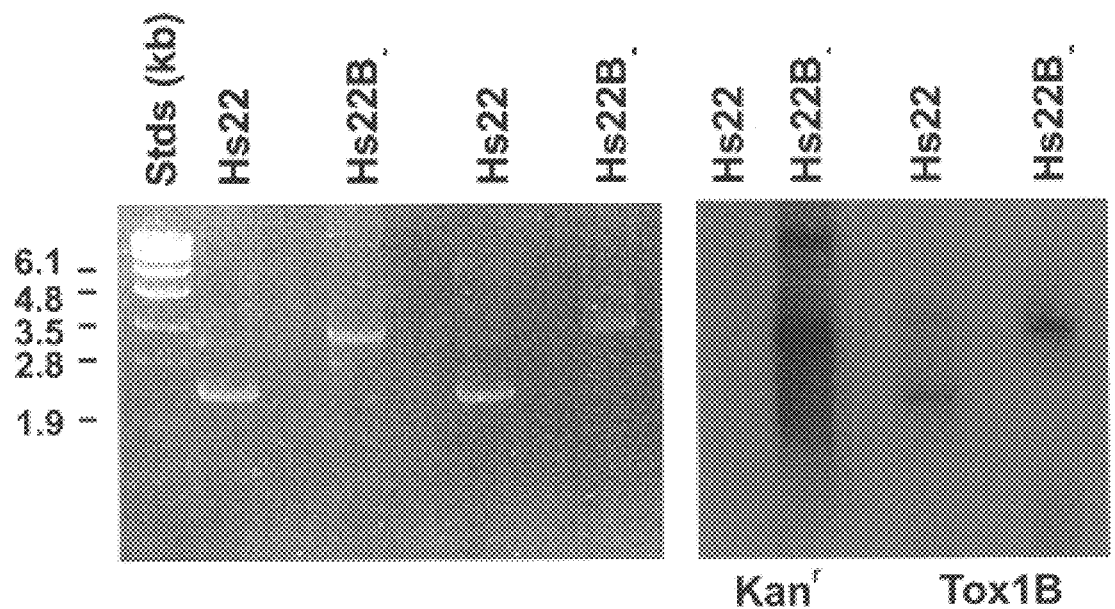

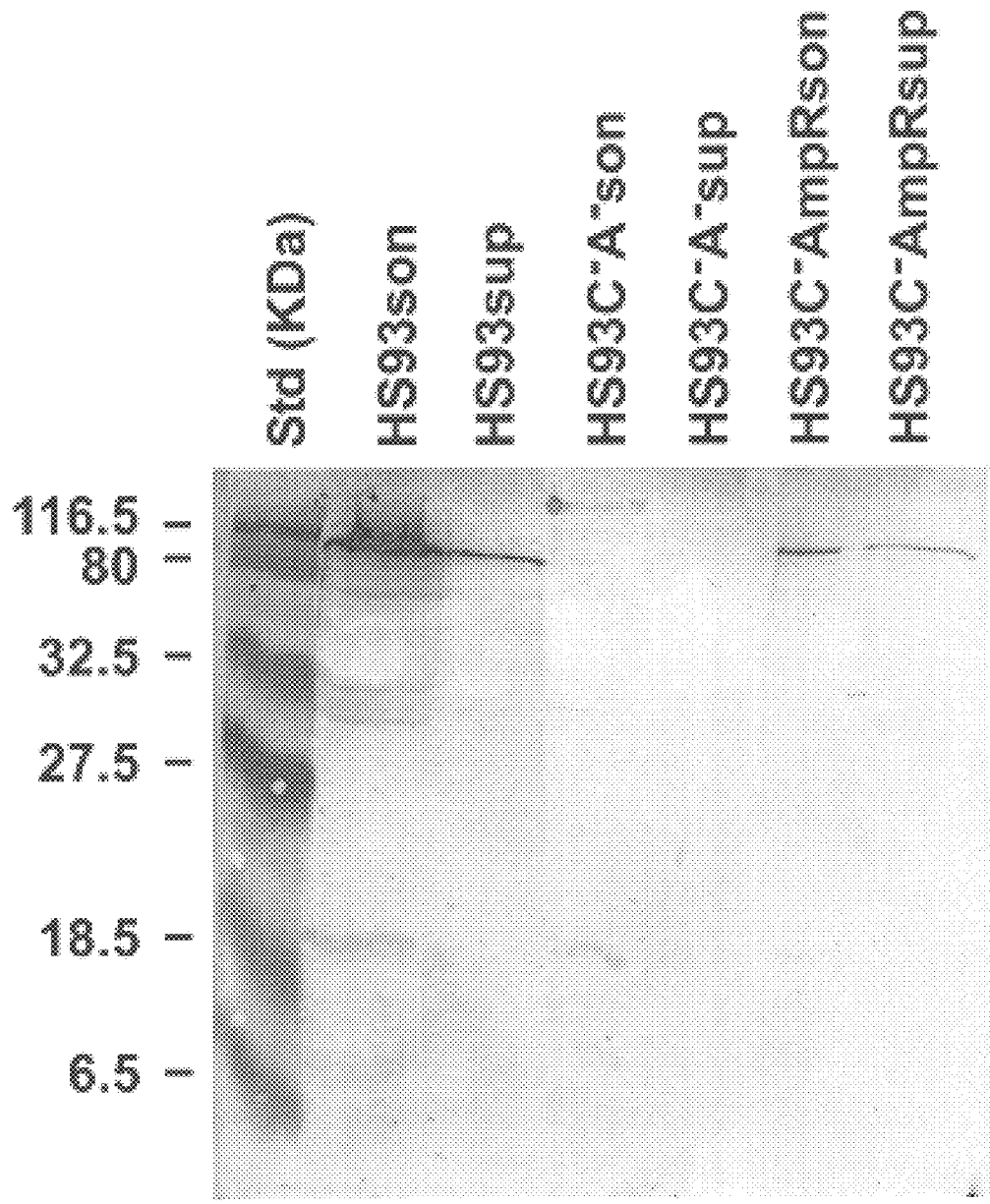

IMMUNITY AGAINST ACTINOBACILLUS PLEUROPNEUMONIAE'S RTX TOXINS APX

The present invention relates to modified microorganisms suitable for use as live vaccines. The present invention also relates generally to the use of modified microorganisms as biological vectors. The present invention further relates to vaccine compositions. In particular, the present invention relates to compositions suitable for inducing an immune response against RTX toxins.

Actinobacillus pleuropneumoniae (APP), is a member of the family Pasteurellaceae, and is the aetiological agent of porcine pleuropneumonia, an acute or chronic infection of pigs characterised by haemorrhagic, fibrinous and necrotic lung lesions (Pohl et. al., 1983; Kilian and Biberstein, 1984). The disease is highly contagious, and associated with all ages of growing pigs, resulting in severe economic losses to the swine industry. The direct mode of transmission of APP means that infection is more prevalent under intensive breeding conditions, fortunately the host range of APP is restricted to pigs reducing the potential sources of infection. To date, twelve serovars of APP have been identified worldwide (Serovars 1–12) with Serovars 1, 7 and 12 making up approximately 90% of Australian isolates (Kamp and Shope, 1964). A number of potential virulence factors have been identified including outer membrane proteins (Mulks and Thacker, 1988; Rapp and Ross, 1988), lipopolysaccharide (Udeze et al., 1987; Fenwick and Osburn, 1986), capsule (Inzana et al., 1988; Rosendale and Macinnes, 1990; Lenser et. al., 1988) and secreted toxins (Rycroft et al., 1991; Bhatia et al., 1991; Fedorka-Crey et al., 1990). The secreted toxins, or APX toxins, are members of the RTX toxin family (Frey et al., 1993, 1994).

RTX toxins are produced by a number of gram negative bacteria including Actinobacillus spp, Proteus vulgaris, Morganella morganii, Bordetella pertussis, Pasteurella haemolytica, and the most characterised of the group produced by E. coli (Welch, 1991). All RTX toxins function by producing pores in the target cells, thereby interrupting osmotic balance, leading to rupture of the target cell. Although the mode of action is identical for RTX toxins their target cells vary greatly in type and cross species specificity. Structurally, this family of toxins are characterised by the presence of glycine rich repeat structures within the toxin that bind calcium and may have a role in target cell recognition and binding, a region of hydrophobic domains that are involved in pore formation, the requirement for post translational activation, and dependence on a C-terminal signal sequence for secretion (Reviewed: Coote, 1992).

At least three different APX toxins are produced by APP, designated APX1, APX2, and APX3. APX1 shows strong, and APX2 relatively low, haemolytic activity, both are cytotoxic and active against a broad range of cells of differing types and species (Frey and Nicolet, 1988; Rosendale et al., 1988; Kamp et al, 1991). APX3 is nonhaemolytic, but is strongly cytotoxic, with a host range including porcine alveolar macrophages and neutrophils (Rycroft et al., 1991; Kamp et al., 1991). No serovar of APP produces all three APX toxins, the majority produce two (APX1 and 2: Serovars 1, 5, 9, and 1 1; APX2 and 3: 2, 3, 4, 6, and 11) with a small number (APX1: 10, APX2: 7 and 12) producing only one APX (Frey and Nicolet, 1990; Frey et al., 1992,1993, 1994; Kamp et al., 1991; Rycroft et al., 1991) The pattern of APX production appears to be associated with virulence, with those serovars producing APX1 and 2 being the most virulent (Frey et al., 1994; Komal and Mittal, 1990). Production and secretion of active RTX toxins requires the activity of at least four genes, C, A, B, and D. The A gene encodes the structural toxin, the C gene encodes the post-translational activator and the B and D genes encode proteins that are required for secretion of the activated toxin (Issartel et al., 1991; Welch, 1991; Felmlee et al., 1985). APX1 and 3 are encoded by operons that consist of the four contiguous genes (CABD), whilst the APX2 operon contains only the C and A genes, and in some cases remnants of the B gene. Secretion of APX2 is dependent on the activity of the APX1B and D gene products (Reviewed Frey et al., 1994).

Virulence analysis of spontaneous, and chemically induced, non-haemolytic mutants indicated a role of the APX toxins in virulence, which has recently been confirmed using transposon mutagenesis (Anderson et al., 1991; Gerlach et al., 1992; Inzana et al., 1991; Rycroft et al., 1991a,b; Tacon et al., 1993, 1994). Complete protection from disease and/ or carrier status cannot be obtained using vaccines comprising chemically inactivated bacteria, or purified subunit vaccines comprising outer membrane proteins, lipopolysaccharides, or capsule. In comparison complete protection from disease in mice was obtained following vaccination with purified APX combined with formalised whole cells, indicating a role for the APX toxins in protective immunity (Bhatia etal., 1991).

Vaccination against pleuropneumonia, resulting from APP infection of pigs, has utilised, to date, bacterins or subunit vaccines based on various components of the bacteria. Results obtained with inactive vaccines have offered, at best, homologous protection against the serovar used to prepare the vaccine material. Currently twelve known serovars of APP exist, of varying virulence, each requiring a different vaccine preparation. To date commercial vaccines have been formulated to contain a number of serovars, offering protection against the most frequently observed serovars in that geographic location. In contrast to inactive vaccines, natural infection with any one serovar offers protection against reinfection with any other serovar, indicating the potential of a live vaccine to offer cross protection against APP serovars.

It is an object of the present invention to alleviate one or more of the problems of the prior art.

Accordingly, in one aspect the present invention provides a modified microorganism which produces an RTX toxin, wherein said RTX toxin is partially or fully inactivated.

The term "modified" includes modification by recombinant DNA techniques or other techniques such as chemical- or radiation- induced mutagenesis. Where recombinant DNA techniques involve the introduction of foreign DNA into host cells, the DNA may be introduced by any suitable method. Suitable methods include transformation of competent cells, transduction, conjugation and electroporation.

In a further embodiment of the present invention, there is provided a modified microorganism wherein an RTX toxin gene including an RTX structural gene and/or a post translational activator of the organism is partially or fully inactivated.

The term "RTX toxin gene" as used herein the claims and description is intended to include those genes involved in the expression of an RTX toxin being a product of the RTX toxin gene. The genes included in the RTX toxin gene include the post translational activator gene (C), the structural gene (a), and the B and D genes which encode proteins that are required for secretion of the activated RTX toxin.

The term "partially or fully inactivated" as used herein the claims and description includes modification of a gene by recombinant DNA techniques including introduction and deletion of DNA from the gene including single or multiple nucleotide substitution, addition and/or deletion including full or partial deletion of the gene, using a target construct or plasmid segregation; and chemical induced-, radiation induced- or site specific mutagenesis.

The present applicants have found that a precursor of an RTX toxin has reduced toxic activity. Surprisingly, the present applicants have also found that the RTX toxin precursor is capable of inducing an immune response in an animal that offers cross protection against heterologous challenge with a microorganism which produces the RTX toxin.

Accordingly, in a preferred embodiment of the invention the inactivated RTX toxin is a precursor of an RTX toxin. The precursor may be an unprocessed expression product of an RTX structural gene. The RTX structural gene may be an RTX A gene.

The microorganism may be one which does not naturally produce an RTX toxin. The microorganism may be a bacterium, virus or fungus into which an RTX structural gene, such as an RTX A gene, has been introduced.

In a preferred embodiment, however, the microorganism is one which naturally produces an RTX toxin. The microorganism which naturally produces an RTX toxin may be selected from Actinobacillus spp, *Proteus vulgaris, Morganella morganii, Bordetella pertussis, Escherichia coli* and *Pasteurella haemolytica*. In a preferred embodiment the microorganism is Actinobacillus spp. The Actinobacillus species may be *Actinobacillus pleuropneumoniae* (APP) and the RTX toxin may be an APX toxin. The APX toxin may be APX1, APX2 or APX3.

The present applicants have found that a microorganism which naturally produces an RTX toxin may be engineered to produce an inactive RTX toxin precursor by eliminating the post-translational activator of the precursor product. Accordingly, in a preferred embodiment the microorganism is unable to produce a post-translational activator of the RTX toxin precursor or produces an inactivated post-translational activator of the RTX toxin precursor. The post-translational activator may be a product of an RTX C gene.

In a preferred embodiment the RTX C gene of the microorganism is inactivated or partially or fully deleted. The RTX C gene may be inactivated by site specific mutagenesis. The RTX C gene may be inactivated by any single or multiple nucleotide substitution, addition and/or deletion. Preferably, the RTX C gene is inactivated by homologous recombination using a targeting construct. The targeting construct may include a selectable marker flanked by sequences homologous to sequences flanking the desired insertion site. The selectable marker may be a gene which confers resistance to a toxic substance such as mercury or may be an antibiotic resistance determinant. The antibiotic resistance determinant may be a gene coding for ampicillin resistance, kanamycin resistance or streptomycin resistance.

In some circumstances it may be undesirable to have a functional antibiotic resistance gene incorporated into a modified microorganism. Accordingly, the present invention contemplates a targeting construct which includes genetic elements, such as repeat sequences, which facilitate excision of the antibiotic resistance gene once the targeting construct has undergone homologous recombination with the host chromosome.

The present invention also contemplates a targeting construct which does not include a selectable marker. For example, the targeting construct may include a segment of the RTX C gene which contains a deletion. Homologous recombination of the targeting construct with the host chromosome may result in the introduction of a deletion into the chromosomal RTX C gene. Selection for recombinants may then be based on the absence of production of the RTX toxin.

The targeting construct may be introduced directly into the host cell in a linear form. Alternatively, the targeting construct may be introduced via a suicide or non-replicating vector. The suicide vector may be any plasmid which does not replicate in the host microorganism. Microorganisms which naturally produce RTX toxins are often non-permissive hosts for pEP vectors. Accordingly, pEP vectors are examples of suicide vectors which may be used in the present invention. The suicide plasmid vector may be pEP-C$^-$Amp$^r$.

In another embodiment, site specific mutagenesis may be achieved by the technique of plasmid segregation. For example, a plasmid which contains a fragment of an RTX C gene interrupted by a selectable marker gene may be introduced to a microorganism. The microorganism may be subsequently transformed with a second plasmid containing a second selectable marker gene. Host cells containing both plasmids may then be passaged through media which selects only for the second plasmid. Selection for the second plasmid may act against maintenance of the first plasmid. The first plasmid may, therefore, be lost, but in some cases recombination of the interrupted RTX C gene fragment containing the selectable marker into the chromosome may occur. This process therefore may encourage recombination of the interrupted RTX C gene into the chromosomal RTX C gene, thus inactivating the chromosomal RTX C gene.

In a further aspect of the present invention there is provided an expression vector which encodes an RTX toxin wherein said RTX toxin is partially or fully inactivated, said vector encoding an RTX toxin gene including an RTX structural and/or post-translational activator gene wherein said RTX toxin gene is partially or fully inactivated.

The term "expression vector" as used herein the claims and description includes a chromosomal or extrachromosomal element which is capable of expressing a DNA sequence including a foreign DNA sequence.

The RTX A gene product may be expressed from a chromosomal RTX A gene. The chromosomal RTX A gene may be located in its natural position on the chromosome or may be inserted into the chromosome at a position other than its natural location. In addition, the RTX gene product may be expressed from an RTX A gene located on an extrachromosomal element such as a plasmid. In one embodiment, therefore, an extrachromosomal element containing an RTX A gene may be introduced to a microorganism which has a functional chromosomal RTX A gene and an inactivated chromosomal RTX C gene. The RTX A product expressed from the extrachromosomal element may supplement the RTX A product expressed from the chromosomal gene.

Alternatively, the RTX A gene product may be expressed entirely from an RTX A gene or genes located on extrachromosomal elements such as plasmids. The RTX A genes located on extrachromosomal elements may be expressed either in the presence or absence of selection for the extrachromosomal element. Thus, in one embodiment an extrachromosomal element containing an RTX A gene may be introduced into a microorganism which lacks functional chromosomal RTX A and RTX C genes. The microorganism which lacks functional RTX A and RTX C genes may be produced by mutagenesis of the microorganism. The mutagenesis may result in deletion of the RTX A and RTX C genes or portions thereof.

The extrachromosomal element may be a recombinant expression vector which includes the RTX A gene. Preferably the recombinant expression vector allows expression of the RTX A gene in microorganisms which naturally produce RTX toxins. The recombinant expression vector may allow expression of the RTX A gene in Actinobacillus or related organisms. The recombinant expression vector may be derived from a plG plasmid. The recombinant plasmid may be derived from plG3B. The recombinant plasmid may be plG3B-TIK.

Bacterial vector systems based on APP (Ph) provide an alternative means to deliver "naked DNA" vaccine molecules to host cells. Such naked DNA vaccine/expression systems would include a plasmid capable of replicating in the bacterial system, and a eukaryotic promoter controlling the expression of the foreign/recombinant gene of interest.

In a preferred embodiment the microorganism is able to produce one or more functional proteins which facilitate secretion of RTX toxin molecules. The microroganism may have functional RTX B and/or RTX D genes. In another embodiment, the microorganism is unable to produce at least one of the proteins involved in secretion of RTX toxin molecules or produces at least one inactive protein involved in secretion of RTX toxin molecules. The microorganism may have an inactive RTX B and/or RTX D gene. Thus, the microorganism may be unable to secrete active or inactive RTX toxin molecules.

In a further aspect the present invention provides a recombinant plasmid vector for expression of heterologous proteins in Actinobacillus or related organisms. In a preferred embodiment the recombinant plasmid vector is derived from a naturally occurring plasmid in *Actinobacillus pleuropneumoniae*. The recombinant plasmid may include a DNA sequence which encodes an RTX toxin precursor. The recombinant plasmid may include an RTX A gene. Alternatively, the recombinant plasmid may include an RTX C gene or a fragment thereof. The RTX C gene or gene fragment may be interrupted by an intervening DNA sequence. The intervening DNA sequence may encode a selectable marker such as an antibiotic resistance gene. The naturally occurring plasmid may be plG3. In a preferred embodiment the recombinant plasmid vector further includes nucleotide sequences which facilitate transfer of DNA to *E. coli*. The nucleotide sequences may include at least one multiple cloning site and lac gene or portion thereof. The recombinant plasmid vector may be selected from plG317, plG3B or plG3B-T1K.

In another aspect the present invention provides a vaccine composition for inducing an immunological response in a host animal inoculated with said vaccine composition, said vaccine composition including an RTX toxin precursor. The RTX toxin precursor may be an unprocessed expression product of an RTX structural gene. The RTX structural gene may be an RTX A gene.

The present invention further provides a vaccine composition for inducing an immunological response in a host animal inoculated with said vaccine composition, said vaccine composition including a modified microorganism which produces an RTX toxin, wherein said RTX toxin is partially or fully inactivated. Preferably the inactivated RTX toxin is a precursor of an RTX toxin. The precursor may be an unprocessed expression product of an RTX structural gene. The RTX structural gene may be an RTX A gene. Preferably, the microorganism is one which naturally produces an RTX toxin. Preferably the RTX C gene of the microorganism is inactivated or deleted.

In a preferred embodiment the vaccine composition which includes a modified microorganism is a live vaccine.

A vaccine composition of the present invention may be incorporated in any pharmaceutically acceptable vehicle with or without added adjuvants or immunostimulatory molecules.

The adjuvant may be of any suitable type. The adjuvant may be selected from vegetable oils or emulsions thereof, surface active substances, e.g., hexadecylamine, octadecyl amino acid esters, octadecylamine, lysolecithin, dimethyldioctadecyl-ammonium bromide, N, N-dicoctadecyl-N'-N'bis (2-hydroxyethyl-propane diamine), methoxyhexadecylglycerol, and pluronic polypols; polyamines, e.g., pyran, dextransulfate, poly IC, carbopol; peptides, e.g., muramyl dipeptide, dimethylglycine, tuftsin; immune stimulating complexes (ISCOMS); oil emulsions; and mineral gels and suspensions. A mineral suspension such as alum, i.e. aluminium hydroxide $(Al(OH)_3)$, aluminum phosphate or aluminium sulphate is preferred. The adjuvant may be present in amounts of from approximately 1 to 75% by weight, based on the total weight of the vaccine composition.

It will be appreciated that a vaccine according to the present invention, which includes an RTX toxin precursor or a microorganism capable of producing an RTX toxin precursor, has the potential to provide protection against a range of serovars of a microorganism which produces the corresponding RTX toxin.

In another aspect the present invention provides a biological vector including a microorganism which naturally produces an RTX toxin, wherein said microorganism has been modified such that it is incapable of producing an active RTX toxin.

The microorganism which naturally produces an RTX toxin may be selected from Actinobacillus spp, *Proteus vulgaris, Morganella morganii, Bordetella pertussis* and *Escherichia coli*. In a preferred embodiment the microorganism is Actinobacillus spp. The Actinobacillus species may be *Antinobacillus pleuropneumoniae* (APP) and the RTX toxin may be an APX toxin. The APX toxin may be APX1, APX2 or APX3. Preferably, the modified microorganism produces an inactive RTX toxin. Preferably, the inactive RTX toxin is a precursor of the RTX toxin. Preferably, the precursor of the RTX toxin is a product of the RTX A gene.

In a preferred embodiment, the modified microorganism is unable to produce a post-translational activator of the RTX toxin precursor or produces an inactivated post-translational activator of the RTX toxin precursor. The post-translational activator may be a product of an RTX C gene. In a preferred embodiment the RTX C gene of the modified microorganism is inactivated or deleted. The RTX C gene may be inactivated by any single or multiple nucleotide substitution, addition andlor deletion.

The RTX C gene may be inactivated by the introduction of a targeting construct containing a selectable marker into the RTX C chromosomal gene through site specific recombination.The targeting construct may include genetic elements, such as repeat units, which facilitate excision of the antibiotic resistance gene once the targeting construct has undergone homologous recombination with the host chromosome. Alternatively, a targeting construct which does not contain a selectable marker may be used to introduce a deletion in the RTX C chromosomal gene.

The RTX A gene product may be expressed from a chromosomal RTX A gene. The chromosomal RTX A gene may be located in its natural position on the chromosome or may be inserted into the chromosome at a position other than its natural location. In addition, the RTX gene product may be expressed from an RTX A gene located on an extrachromosomal element such as a plasmid. Alternatively, the RTX A gene product may be expressed entirely from an RTX A gene or genes located on extrachromosomal elements such as plasmids.

In a preferred embodiment the microorganism is able to produce one or more functional proteins which facilitate secretion of RTX toxin molecules. The microroganism may have functional RTX B and/or RTX D genes. In another embodiment, the microorganism is unable to produce at least one of the proteins involved in secretion of RTX toxin molecules or produces at least one inactive protein involved in secretion of RTX toxin molecules.

The term "biological vector" is used in its widest sense to include a biological means suitable for expression of biologically active molecules. The biological means is preferably a viable microorganism although dead organisms could be employed. The biological vector may be non-pathogenic or rendered avirulent or may be given in non-pathogenic or avirulent effective amounts. The term "biologically active molecules" includes functional molecules such as growth factors, hormones, enzymes, antigens or antigenic parts thereof, cytokines such as interleukins, interferons and tumor necrosis factors. The molecules may be expressed naturally by the biological vector. Alternatively, the molecules may be recombinant molecules expressed by transforming the biological vector with a plasmid carrying a gene or genes encoding the biologically active molecule and which is then expressed; or where the plasmid and/or gene or genes and/or parts thereof are integrated into the host genome, which includes the chromosome and/or any naturally or non-naturally occurring extra-chromosomal element, wherein the gene or genes or parts thereof are expressed.

It will be appreciated that a biological vector of the present invention may be used to provide one or more useful proteins to the host animal. The proteins so provided may act in synergy to bring about an enhanced reaction in the host animal. For example, the biological vector may produce an antigen in combination with a molecule which enhances an immunogenic response in the host animal to the antigen. The molecule which enhances the immunogenic response may be a cytokine.

It will also be appreciated that a biological vector of the present invention may be used to provide a multivalent vaccine. The term "multivalent vaccine" is used in its most general sense and extends to a modified microorganism capable of inducing an immune response to two or more distinct antigenic epitopes on or expressed by the modified microorganism where the two or more epitopes are indigenous to the modified microorganism. More commonly, however, a multivalent vaccine includes a modified microorganism capable of inducing an immune response to virulent forms of said microorganism as well as to heterologous antigens expressed by said microorganism (such as recombinant antigens or those introduced by transduction, conjugation or transformation) and which are not indigenous to the microorganism. In this regard, a multivalent vaccine may be directed to two or more pathogenic agents. Preferred multivalent vaccines are those capable of inducing an immune response against an RTX toxin and to at least one antigenic eptiope from one or more pathogenic agents. The pathogenic agents may be selected from bacterial pathogens such as Haemophilus spp, *Serpulina hyodysentedae*, Pasteurella spp, *Bordetella bronchiseptica*, Leptospira spp, Streptococcus spp, Salmonella spp, *Escherichia coli, Mycoplasma hyopneumoniae, Erysipelothrix rhusiopathiae*. Alternatively, the pathogenic agents may be selected from viral pathogens such as HCV, PRRSV, PRV, TGEV, PPV.

The present invention further provides a method of producing a modified organism which produces an RTX toxin which is partially or fully inactivated which method includes providing a microorganism which produces an active RTX toxin; and inactivating or deleting the RTX C gene.

The present invention further provides a method of producing a modified organism which produces an RTX toxin which is partially or fully inactivated which method includes providing a microorganism which is incapable of producing an active RTX toxin; and introducing a functional RTX A gene into said microorganism.

The invention in yet a further aspect provides a method for vaccinating an animal against an RTX toxin producing microorganism, said method including administering to said animal an immunologically effective amount of a vaccine in accordance with the present invention.

The method of vaccination may be utilised in the treatment of production animals such as pigs, cattle, sheep, goats. The method of vaccination may also be used in the treatment of companion animals such as horses, dogs and cats. The method of vaccination may also be used in the treatment of humans. In a preferred embodiment the method of vaccination is utilized in the treatment of pigs. Preferably the method of vaccination is utilized in the treatment of porcine pleuropneumonia.

Administration of a vaccine or vaccine vector in accordance with the present invention may be by any suitable route such as by oral or parenteral administration. The administration may be mucosal such as nasal or vaginal. Alternatively, administration may be intramuscular, intradermal, subcutaneous or intraperitoneal. The preparation may be in dry or liquid form. The route of administration chosen may also necessitate additional components such as protease inhibitors, anti-inflammatories and the like.

The invention in yet a further aspect provides a method for vaccinating an animal against a pathogenic organism, said method including administering to said animal an effective amount of a vaccine vector in accordance with the present invention wherein said vaccine vector synthesises an immunologically effective amount of an antigen of said pathogenic organism.

In yet another aspect the present invention provides a method for the production of an inactive RTX toxin which method includes culturing a modified microorganism in accordance with the present invention and recovering the inactive toxin produced by said microorganism. The inactive RTX toxin produced by this method may, for example, be used as the active immunogen in a vaccine for stimulating a protective immune response against an RTX toxin.

Throughout the description and claims of this specification, the word "comprise" and variations of the word, such as "comprising" and "comprises", is not intended to exclude other additives, components, integers or steps.

In order that the invention may be more readily understood we provide the following non-limiting examples.

BRIEF DESCRIPTION OF THE FIGURES

FIG. 1B) was found to be sufficient to encode plasmid replication and confer streptomycin resistance when self ligated, and transformed into *E. coli* of APP. The plasmid vector plG3B, containing a multiple cloning site (MCS) and a portion of the lac gene, was constructed by introducing the HaeII fragment of plC19R into the unique EcoRI site of plG317 (FIG. 1C). Unique restriction enzyme sites are indicated for plG3B (FIG. 1C), with the exception of PstI which cuts in the MCS and plasmid backbone.

FIGS. 6A–6B. The polymerase chain reaction (PCR) was used to characterise the chromosomal mutants, HS22B⁻Kan$^r$ (FIG. 6A) and HS93C⁻Amp$^r$ (FIG. 6B). Genomic DNA from each of the mutants was isolated and used as the template for PCR. Oligonucleotides that spanned the site of insertion (FIG. 5) produced single bands corresponding to the predicted size for each of the parent strains and the genomic mutants. Each of the mutants produced a PCR product larger, corresponding to an increase in size equivalent to the antibiotic resistance gene inserted, than that of the parent strain. The PCR produces obtained were southern-blotted and probed with either the APX gene targeted for insertion or the antibiotic resistance gene utilised for selection.

FIG. 7. Secreted proteins (sup), and total culture proteins (son), of the APP Tox$^-$ strain (HS93C$^-$A$^-$), and the HS93C$^-$Amp$^r$ mutant were examined by western-blotting along side the parent strain HS93. The blot was probed with rabbit anti-sera, produced within our laboratory, against the APX toxins. From the figure it can be seen that the Tox$^-$ strain does not react with anti-APX sera, whilst both the parent strain, HS93, and the HS93CAmp$^r$ recombinant produce single polypeptides that are secreted and react specifically with the sera.

FIGS. 8A–8B. plG Based Cassettes for the Expression of Foreign Proteins in APP. A series of plG based expression cassettes were constructed for the expression of foreign proteins from APP. The genes encoding foreign proteins, IL6 (FIG. 8A) and CAT (FIG. 8B) were cloned along side suitable promoters, in plG based plasmids, to enable expression in APP.

FIG. 9. Expression of Porcine IL6 from APP. Porcine IL6 was cloned into a suitable plasmid vector (plG-IL6) to obtain expression in *E. coli* (*E. coli*/plG3-IL6) and APP (HS93/plG-IL6). Samples of overnight cultures of APP HS93 (1), APP HS93/plG-IL6 (2), *E. coli*/plG-IL6 (3 and 4), purified IL6 (5 and 6), together with a negative *E. coli* control (7) were analysed by western blotting using monoclonal antibodies specific to IL6.

EXAMPLE 1

Materials and Methods

Bacterial Strains and Growth Conditions

The APP bacterial strains used in this study were kindly supplied by Dr. Pat Blackall (Animal Research Institute, Moorooka, QLD, Aust.). Strains of APP were grown in brain heart infusion broth supplemented with nicotinamide adenine dinucleotide at an end concentration of 10 $\mu$g/ml (Sigma Chemical Co., St. Louis, Mo.), at 37° C. with continuous shaking. Blood agar was prepared by adding 5% sterile defibrinated horse red blood cells to the BHI agar. Antibiotics were used at a final concentration of Kanamycin 25 $\mu$g/ml, Streptomycin 50 $\mu$g/ml, or Ampicillin at 5 $\mu$g/ml, unless stated differently in the text. The *E. coli* strain DH5$\alpha$ was used throughout this study, using standard techniques as outlined in Sambrook et al., (1989).

Isolation of APP Genomic DNA

Bacteria present in 1 ml of an overnight culture of APP HS25, grown in BHI supplemented with AND (IO $\mu$g/ml) were collected by centrifugation, and the supernatant discarded. The pellet was resuspended in 1 ml of TE (IO mM Tris-HCl pH8.5/1 mM EDTA), containing lysozyme (7.5 mg/ml), and incubated at 37° C. for 2 hr, after which the solution was adjusted to a final concentration of 0.1 M NaCl, 1% SDS and 2.5 $\mu$g/ml ProteinaseK, and incubation continued overnight at 50° C. The following day the preparation was adjusted to 0.5M NaCl and extracted twice with phenol/chloroform/isoamyl alcohol (100:99: 1, v/v/v), the genomic DNA was then precipitated by the addition of 0.6 volumes of isopropanol. ps Isolation and Cloning of the APX1A Gene Amplification of the APx1A gene was performed using the polymerase chain reaction (PCR). Reactions were performed in 50 $\mu$l volumes comprising 50 $\eta$g of APP genomic DNA (HS25), 3 $\eta$g of oligonucleotide primer, 50 mM KCl, 10 mM Tris-HCl, pH8.3, 2.5 mM $MgCl_2$, 200 mg/ml BSA, 200 mM of each dATP, dCTP, dGTP, and dTTP, plus 1 unit of Taq DNA polymerase (Perkin Elmer Cetus, USA). Reactions were overlayed with an equal volume of paraffin oil and heated to 94° C. for 1 min, cooled to 55° C. for 2 min and heated to 72° C. for 5 min. This cycle was repeated 35 times using a Perkin-Elmer-Cetus DNA thermal Cycler. Specific oligonucleotides were designed based on the published sequence of the APX1 gene (Frey et al., 1991)). The sequence of the two oligonucleotides was 5'GGA GGA TCC ATG GCT MC TCT3' (SEQ ID NO: 7) and 5'ACC TAC CCG GGA TAG GAT TGC TAT TT3' (SEQ ID NO: 8) , and were designed to produce a PCR product with a BamHl site at the 5', and a SmaI site at the 3' ends to facilitate cloning. The oligonucleotides were synthesised using a gene Assembler Plus DNA Synthesiser (Pharmacia, Sweden). Products of PCR reactions, corresponding to the predicted molecular weight of the APX1 gene were isolated from agarose gels by gene cleaning (BRESATech, Australia), restriction enzyme digested with BamHI and SmaI, and cloned into the BamHI and SmaI sites of pUC18 (Yanish-Perron et al., 1985). Confirmation of clones containing the APX1 gene was achieved by double stranded sequencing (results not shown).

Figure 1A:
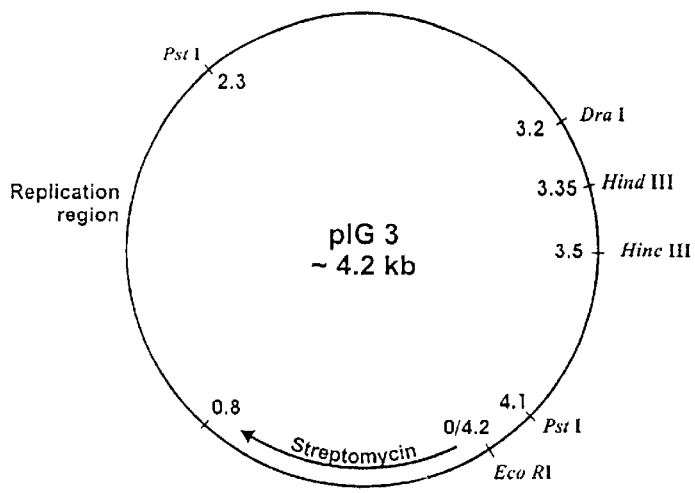
FIGS. 1A–1C. partial restriction enzyme map of plG3 (FIG. 1A), a 4.2 kb plasmid encoding streptomycin resistance, isolated from an Australian strain of APP. A 2.3 kb PstI fragment (plG317.

Isolation of the APX1A Gene from the Chromosome of APP

Based on published data the 3 ' 2 kb of the APX1A gene is encoded on a HindIII fragment of approximately 5 kb (Frey et al., 1993). In order to isolate this fragment, APP HS25 genomic DNA was digested to completion with the restriction enzyme HindIII and size fractionated on an agarose gel. Digested DNA was visualised by ethidium bromide staining and the region corresponding to approximately 5 kb, as estimated using DNA molecular weight standards (Progen, Australia), excised and the DNA purified using gene clean (BRESAtech, Australia). The size selected genomic DNA was cloned into pUC18 and transformed into E. coli. The resulting E. coli library was probed with the APX1A PCR fragment and positive clones selected. Restriction enzyme digests were used to confirm the authenticity of clones identified by hybridisation.

Transformation of APP with Plasmid Vectors

The preparation of electrocompetent APP, and the conditions for introduction of plasmid DNA into these cells by electroporation (0.2 cm cuvettes, 400SL, 1.25 kv and 25 $\mu$F) was as described by Frey (1992), with the exception that 200 $\mu$l aliquots of competent cells were used for electroporation. Plasmid DNA was isolated from overnight cultures of APP, grown under antibiotic selection, using magic minipreps (Promega).

Isolation of Regions of the APP Chromosome Using PCR

Amplification of regions of the APP chromosome was performed using the polymerase chain reaction (PCR). Reactions were performed in 50 $\mu$l volumes comprising 50 ηg of genomic DNA, 3 ηg of oligonucleotide primer, 50 mM KCl, 10 mM Tris-HCl, pH8.3, 2.5 mM MgCl$_2$, 200 mg/ml BSA, 200 mM of each dATP, dCTP, dGTP, and dTTP, plus 1 unit of Taq DNA polymerase (Perkin Elmer Cetus, USA). Preparation of APP genomic DNA was as described in Prideaux et al. (1995), using SDS and proteinaseK. Reactions were overlayed with an equal volume of paraffin oil and heated to 94° C. for 1 min, cooled to 55° C. for 2 min and heated to 72° C. for 5 min. Specific oligonucleotides were synthesised using a gene Assembler Plus DNA Synthesiser (Pharmacia, Sweden). Products of PCR reactions were resolved on agarose gels and visualised by staining with ethidium bromide.

Mutagenesis of the APP Chromosome within the APX1B Gene

The recombination plasmid pIG3-BK$^r$, designed for inactivation of the APX1B gene, was electroporated into APP HS22 as described by Prideaux et al. (1997), and transformants selected on BHI/AND agar containing Kanamycin. APP transformants containing the recombination plasmid were then electroporated with pIG3-Amp$^r$, isolated from APP, and the transformants selected on BHI/AND plates containing Kanamycin and Ampicillin. The presence of both plasmids was confirmed by reisolating plasmids, using magic miniprep protocols (Promega), ana pertorming restriction enzyme analysis. A transforrnant containing both plasmids was grown overnight with shaking in BHI/AND containing Ampicillin and Kanamycin. The culture was diluted 1:100 in 10 ml BHI/AND containing Ampicillin (50 $\mu$g/ml) and shaken overnight. The subculturing procedure was repeated a total of 6 times, after which dilutions of the culture were plated onto BHI/AND blood agar plates containing Kanamycin. Colonies that did not produce zones of haemolysis on blood agar plates were identified and isolated for further characterisation.

Southern Blot Analysis of PCR Products

Products of PCR reactions were resolved on 1% agarose gels, along side DNA molecular weight markers (Progen, Australia) to allow size estimations to be performed, after staining with ethidium bromide. The fractionated DNA was transferred to Hybond-N membrane (Amersham) using a vacuum blot system (Pharmacia) according to the manufactures instructions. Membranes were hybridised overnight at 65° C. in buffer containing 5×SSPE (1×SSPE: 0.18M NaCl, 10 mM Sodium phosphate, ImM EDTA, pH7.7), 5×Denhardt's solution (1×Denhardt's: 0.02% BSA, 0.02% Ficoll, and 0.02% polyvinylpyrrolidone), and 0.5% SDS. Probes for hybridisation were labelled using the random hexamer primer system (BRESAtech, Adelaide, Australia), according to the manufacturers instructions. After hybridisation membranes were washed to a final stringency of 0.1% SDS/0.1×SSPE at 65° C. for 10 min, and exposed to X-ray film (Fuji RX).

Production of Antisera

Overnight cultures of APP HS25 were diluted 1 in 20 and grown at 37° C. with shaking until an OD$_{600}$ of 0.8 was reached. At this point, cultures were centrifuged at 12,000 rpm for 12 min at 4° C., and supernatant proteins purified using the method of Fedorka-Cray et al. (1990). Rabbits were given a total of three doses of purified protein (IOO $\mu$g) at two week intervals, the first of which was in Freund's Complete adjuvant, with subsequent vaccinations in Freund's Incomplete adjuvant. Sera was collected for use two weeks following the final boost.

Western Blot Analysis

Western blot (immunoblot) analysis was performed by the method of Sambrook et al. (1989). Rabbit sera produced against culture supernatant proteins of APP HS25 was used for the detection of APX proteins at a 1:50 dilution. The rabbit sera was pre-absorbed against APP Tox$^-$) to remove cross reacting, and non-APX antibodies before use. The conjugate, used at a 1:1000 dilution, was Sheep anti-rabbit 1 g affinity isolated HRP conjugated antisera (Silenus) with tetramethylbenzidine (McKimm-Breschkin, 1990) as the substrate. Bacterial samples for western blot analysis were prepared by diluting overnight cultures 1 in 20 in the appropriate growth media, and incubating at 37° C. with vigorous shaking until an OD$_{600}$ of 0.8 was reached. At this point samples containing 20 $\mu$l of total culture were analysed by SDS-PAGE, and proteins were transferred to nitrocellulose (Bio-Rad) by using a Bio-Rad Transblot Cell as described in the manufacturer's specifications.

Vaccination and Challenge of Mice

Six week old female Balb-C mice, obtained from the Walter and Elisa Hall Institute of Medical Research (Parkville, Vic), were maintained at CSIRO Division of Animal Health (Parkville, Vic, Australia) under PC2 facilities with water and food ad libitum. Mice were injected intraperitoneally (IP) with 200 $\mu$l of APP preparation on days 0 and 14, and received an IP challenge on day 28. Control mice received 200 $\mu$l of BHI broth IP. The number of mice surviving for 24 hrs following challenge were recorded, and were considered to have been protected from challenge or received a sublethal dose.

Antibody Assay

All mice were bled from the tail prior to vaccination and prior to boosting, or challenge. Antibody responses to APX IA or 2A were measured by an indirect enzyme-linked immunosorbant assay (ELISA) with 0.5 ug of poly-His purified APX per well as described by Prideaux et al., (1995). Titers are expressed as the maximum dilution that still gave optical densities greater than sera from untreated mice.

EXAMPLE 2

Development of a Plasmid Vector for APP

A survey of 14 APP strains (Provided by Dr. Pat Blackall; Animal Research Institute, Moorooka, QLD, Aust.) identified two strains harbouring plasmids that could be detected using magic miniprep plasmid isolation (Promega) combined with agarose gel/ethidium bromide detection (results not shown). One of these strains, HS205, was found to be streptomycin resistant, plasmid DNA isolated from this bacteria was found to confer streptomycin resistance to both E. coli and APP when introduced by electroporation.

Figure 1B:
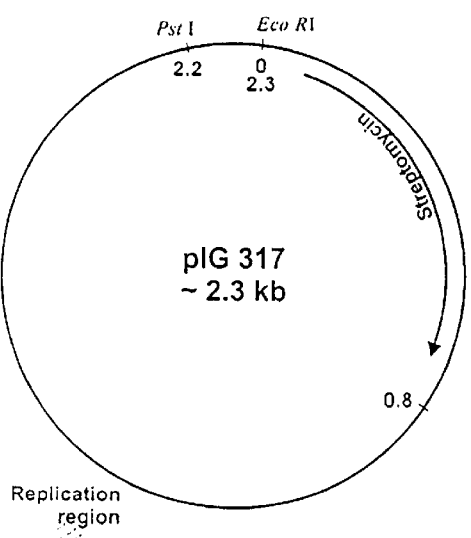
Figure 1C:
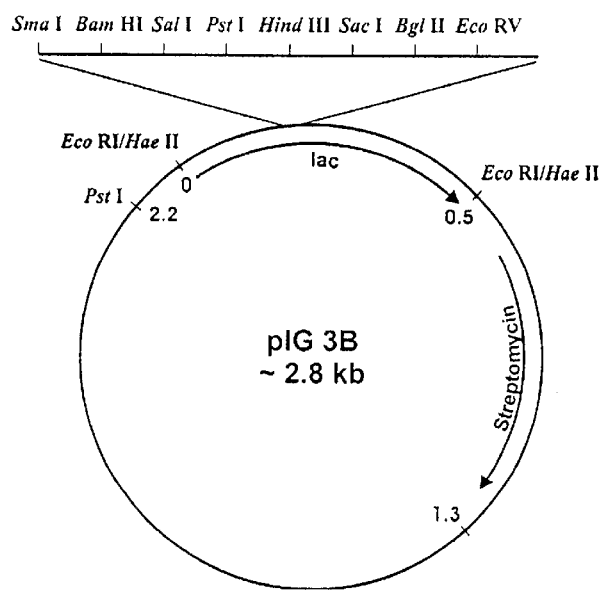

Restriction enzyme analysis of plasmid DNA isolated from E. coli that had been transformed with plasmid DNA isolated from HS205 and selected on streptomycin, identified a 4.2 kb plasmid (pIG3) that encodes it's own replication and streptomycin resistance (FIG. 1 A). A restriction enzyme map was generated for pIG3, and by a process of restriction enzyme digestion and ligation it was found that when a 2.3 kb PstI 0 sub-fragment of pIG3 was self ligated (pIG317), and transformed into E. coli, the resulting transformants were streptomycin resistant (FIG. 1B).

To increase the versatility of this plasmid to carry foreign DNA into both E. coli and APP, the 450 bp HaeII fragment from pIC19R, containing the multiple cloning site and lac gene (Marsh et al., 1984), was sub-cloned into the unique EcoRI site of pIG317, located 300 bp down stream of the PstI site (pIG3B; FIG. 1B). The resulting plasmid, pIG3B (FIG. 1C), has a multiple cloning site suitable for insertion of foreign DNA into the plasmid, and a lac gene to allow rapid selection of plasmids carrying foreign DNA based on blue/white selection in the presence of X-gal in E. coli.

EXAMPLE 3

Expression of the APX1A Gene in E. Coli

Figure 2:
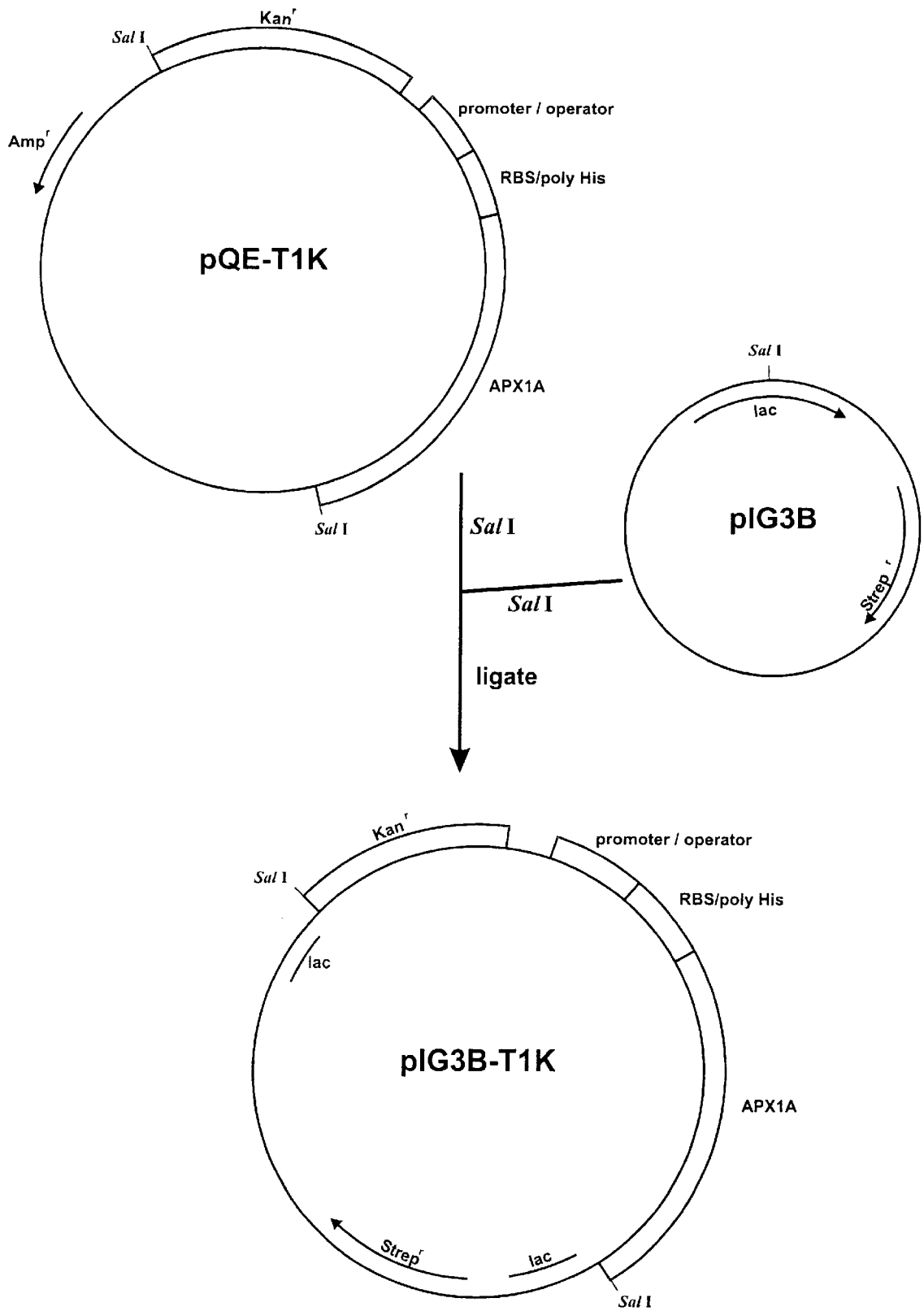
FIG. 2. Construction of an APX1A expression cassette for use in APP. The APX1A expression cassette, linked to the kanamycin resistance gene, from pQE-T1K, was isolated as a SalI restriction enzyme fragment and cloned into the unique SalI site of plG3B. Not all unique restriction enzyme sites in the multiple cloning site of plG3B are indicated.

In order to minimise any errors that might have been introduced into the APX1A open reading frame (ORF) during PCR, and to allow correct alignment of the ORF within the expression vector, the genomic fragment was used in conjunction with the PCR fragment to construct the expression plasmid pQE-TI as outlined in FIG. 2. This strategy enabled the APX1A ORF to be inserted into pQE30 (QIAGEN Inc., Chatsworth, Calif., USA.) in frame with the poly-His purification signal, and to consist of a majority of genomic DNA.

Expression of APX1 A from pQE-T1 was under the control of a regulable promoter/operator element, consisting of the E. coli phage T5 promoter and two lac operator sequences. Optimal expression of APX1A from pQE-TI was achieved by growing an overnight culture of E. coli containing the expression vector in the presence of ampercillin (100 $\mu$g/ml). The following day a 1 in 50 dilution of the culture was made, and incubated at 37° C. with vigorous shaking until an $OD_{600}$ of 0.8 was reached. At this time induction of the toxin was achieved by adding IPTG to a final concentration of 2 mM and the culture grown for a further 5 hours, after which the E. coli was collected by centrifuging at 8,000 rpm for 12 min.

Purification of APX1A was achieved using immobilised Ni chelate affinity chromatography under denaturing conditions, as per the manufacturers instructions (QIAGEN Inc., California, USA). This system takes advantage of the 6-His tag present on proteins expressed using the pQE system.

EXAMPLE 4

Construction of an APX1A Expression Cassette for APP

Figure 3:
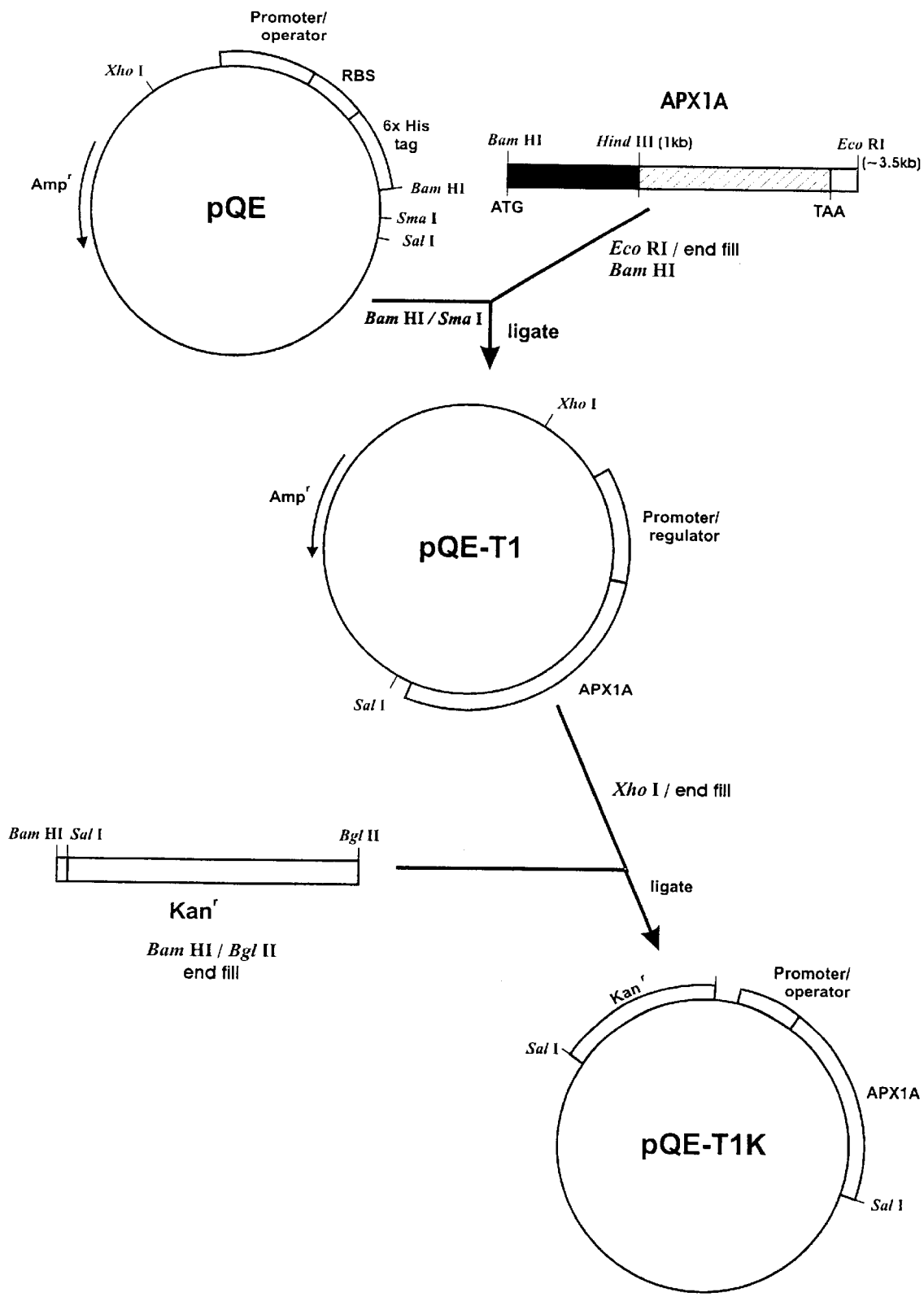
FIG. 3. Construction of APX1 expression cassette for *E. coli*. A complete APX1A gene was procured by fusing PCR derived (■) material, and a genomic clone ( ) at a unique HindIII site. The complete gene was cloned into pQE, inframe with the polyHIS leader sequence to allow APX1A purification. The kanamycin resistance gene from pUC4K, was cloned into a unique XhoI restriction site 5' of the pQE-T1 promoter/regulator sequences. The resulting plasmid, pQE-T1K, contains the APX1A gene, under regulated expression, linked to the kanamycin resistance gene.

To facilitate the construction of pIG based APXI expression cassettes, the kanamycin resistance gene was isolated from pUC4K (Pharmacia) and shuttled through pIC20R before being cloned into pQE-TI as outlined in FIG. 3. The resulting plasmid, pQET1K, contained the Kanamycin resistance gene and APX1A gene, linked to the T5 promoter, both flanked by SalI restriction enzyme sites. The SalI fragment was isolated and ligated with pIG3B, which had been previously digested with SalI, and transformed into E. Coli. The desired clone was identified by selecting transformants which were Kanamycin resistant and produced white colonies in the presence of X-GaI. Plasmid DNA was isolated and restriction enzyme analysis used to confirm the predicted profile of pIG3B-TIK (FIG. 3).

EXAMPLE 5

Construction of the APP Vaccine Strain

During a process of site specific mutagenesis of the HS93 APP (Serovar7; APX2 production only) chromosome, designed to delete a small portion of the APX2C gene, an isolate was obtained that failed to produce a zone of haemolysis on blood agar plates. Further characterisation of this isolate (APP Tox⁻) showed it to be missing a large portion of the chromosome surrounding the intended site of deletion. The resulting APP Tox⁻ strain contains no APX structural, or activating genes, though still produces the necessary proteins required for APX secretion, as these genes are located elsewhere on the APP chromosome.

The APP Tox⁻ strain was transformed with pIG3B-TIK as described in materials and methods using kanamycin selection. Plasmid DNA was isolated from kanamycin resistant colonies and analysed by restriction enzyme digestion to confirm the predicted profiles of pIG3B-TIK.

EXAMPLE 6

Characterisation of the APP Vaccine Strain

Overnight cultures of the APP Tox⁻ stain containing pIG3B-TIK, as well as the APP Tox⁻ strain and HS93, were examined by western blotting using antisera raised in rabbits against the secreted proteins of HS25 (ie APX1 and 2). From the western blot (FIG. 4) it can be seen that the APP Tox⁻ strain did not bind any antibodies present in the sera, while both wild type HS93 and APP Tox⁻/pIG3B-TIK both have a single band. The band detected with Tox⁻)/pIG3B-TIK is larger than that seen with its parent strain, HS93, as the parent strain expresses APX2 (apparent Mw of 103–105 kDa), whilst Tox⁻/pIG3B-TIK produces APX1 (apparent Mw of 105–110 kDa).

EXAMPLE 7

Comparison of Virulence of APP Strains in Mice

Overnight cultures of APP HS93, HS25 and Tox⁻ were grown with vigorous shaking at 37° C. in BHI broth supplemented with AND (10, µg/ml). The following day a 1 in 20 dilution of the cultures was made, and the new cultures incubated until an $OD_{600}$ of 0.8 was reached, at this $OD_{600}$ value the viable count of APP is $1\times10^9$ per ml (data not shown). Various dilutions of the cultures were prepared in BHI broth supplemented with AND (10 µg/ml) and 200 µl administered to mice IP. Following challenge mice were observed, and total deaths recorded after 24 hours. Under our conditions no mice succumbed to APP infection after this period, the results obtained are presented in Table 1. A comparison of the deaths obtained with each serovar would indicate that HS25, which belongs to Serovar 1 and produces both APX1 and 2, is the most virulent APP strain (100% death at $1\times10^7$), followed by HS93 (100% death at $2\times10^8$), which belongs to Serovar 7 and produces APX 2 only, whilst the Tox⁻ (Serovar7) strain failed to kill any mice even at the highest dose used. This result is in agreement with observations from pleuropneumonia out breaks in pigs where the most severe out breaks are associated with APP serovars that produce APX1 and 2.

TABLE 1

Virulence of APP Strains in Mice

| Challenge level (x 10⁶) | PERCENT OF DEATHS | | |
|---|---|---|---|
| | HS25 | HS93 | Tox⁻ |
| 200 | | 100 | 0 |
| 20 | 100 | 15 | |
| 10 | 100 | 0 | |
| 4 | 33 | | |
| 2 | 0 | | |

Table 1. Mice were injected with 200 µl of bacterial suspension containing various levels of APP strains, HS25, HS93 or the Tox⁻ strain. Deaths were recorded after 24 hrs and are expressed as percentage of total population.

EXAMPLE 8

Protection of Mice from Lethal APP Challenge

Overnight cultures of HS93 and Tox⁻ were prepared and the following day a 1 in 20 dilution made and grown to an $OD_{600}$ of 0.8. Dilutions of each bacteria were made so that a 200 µl vaccination contained either $2\times10^7$ HS93, or $2\times10^8$ Tox⁻, these values were chosen to maximise vaccination dose, but still maintain a sub-lethal challenge, control mice received 200 µl of BHI broth. Mice were vaccinated IP at days 0 and 14 and challenged with either $1\times10^8$ HS25 or $5\times10^8$ HS93 at day 28, and deaths recorded after 24 hours (Table 2). From these results it can be seen that both HS93 and Tox⁻) offered complete protection against homologous challenge, whilst HS93 offered some protection against heterologous challenge. The Tox⁻) strain offered no protection against heterologous challenge, which is also observed with bacterin based inactivated vaccines, indicating a role for APX toxins as cross serotype protective antigens.

To assess the ability of APP Tox⁻) expressing the unactivated form of APX1 from a plasmid to protect mice against a lethal heterologous challenge of APP, mice were vaccinated with APP Tox⁻ or APP Tox⁻/(plG3B-TIK according to the following schedule. On day 1 mice were bled from the tail and then vaccinated IP with 200 µl of BHI containing $2\times10^8$ Tox⁻ or Tox⁻/plG3B-TIK. The procedure was repeated on day 14 and on day 28 mice were bled from the tail, and challenged with 5×108, or $1\times10^8$, APP HS25. Sera collected from mice were used in an ELISA to measure antibodies directed against APX1 as outlined in materials and methods. Control sera was collected from mice that had received two doses of HS93 ($2\times10^8$) or HS25 ($2\times10^6$) IP at two week intervals.

The ELISA results presented in Table 3 indicate that a single dose of Tox⁻/plG3B-T1K is sufficient to produce a good antibody response in mice, equivalent to that obtained following two doses of HS25, at a reduced level. The anti-APX1 response was boosted considerably following a second vaccination with Tox⁻(/plG3B-TIK, whilst multiple vaccinations with HS93 or Tox⁻ did not produce antibody values above background. The inability to detect antibodies that recognised APX1 following multiple vaccinations with HS93, which produces APX2, would indicate an inability for antibodies directed against APX2 to cross react with APX1, this is in contrast to the ability of HS93 expressing APX2 to offer a degree of protection against heterologous challenge and may reflect the difference between E. coli expressed Ag and APP derived.

Mice challenged with 10 $ID_{50}$ of HS25 showed no protection following vaccination with Tox⁻, whilst those vaccinated with Tox⁻)/plG3B-TIK demonstrated a 60% protection. When the challenge level was reduced to 5 $ID_{50}$ of HS25, once again no protection was observed with Tox⁻ alone whilst Tox- expressing the APX 1A gene from a plasmid (Tox⁻/plG3B-TIK) demonstrated 100% protection (Table 4).

TABLE 2

Vaccination of Mice with APP Tox⁻

| | PERCENT OF DEATHS | | |
|---|---|---|---|
| Challenge Strain | Control | Tox | H593 |
| H593 ($2 \times 10^8$) | 100 | 0 | 0 |
| HS25 ($1 \times 10^8$) | 100 | 100 | 30 |

Table 2. Mice were vaccinated twice with $2\times10^8$ APP Tox⁻ or $2\times10^7$ of the parent strain HS93, intraperitoneally, at two week intervales and then challenged two weeks later with HS93 (homologous) or HS25 (heterologous). Control mice received 200 1 of BHI broth. Deaths following challenge were recorded as the percentage of mice within each group that died within 24 hr.

TABLE 3

Induction of APX1A Specific Antibodies in Vaccinated Mice

| Inoculation | APX1A Antibody Titre |
|---|---|
| Single Vaccination | |
| Tox⁻ | 3,000 |
| Tox⁻/pIG3B-T1K | 25,000 |
| Two Vaccinations | |
| Tox⁻ | 3,000 |
| Tox – /pIG3B-T1K | >200,000 |
| HS93 | 3,000 |
| HS25 | 25,000 |

Table 3. Mice were vaccinated twice with $2\times10^8$ Tox⁻ or Tox⁻/pIG3B-T1K IP at two week intervals and, sera was collected prior to, and two weeks after boosting. Control mice received two doses of $2\times10^7$ HS93 or $2\times10^6$ HS25. APX1A specific antibodies were measured in an ELISA, and the titre expressed as the reciprocal of the last dilution that gave absorbance values greater than back ground.

TABLE 4

Protection of Mice Against Heterologous Challenge with APP following Vaccination with Tox⁻/pIG3B-T1K

| Challenge HS25 | Vaccine Strain | | |
|---|---|---|---|
| | Controls | Tox⁻ | Tox⁻/pIG38-T1K |
| 10 ID$_{50}$ % Protection | 0 | 0 | 60 |
| 5 ID$_{50}$ % Protection | 0 | 0 | 100 |

Table 4. Mice were vaccinated intraperitoneally, twice at two week intervals, with the Tox⁻ strain of APP with, and without, the plasmid plG3B-T1K, which encodes the expression of the APX1A protein. Control mice received two doses of BHI broth. Two weeks following the final vaccination mice were given a heterologous challenged of APP HS25.

EXAMPLE 9

Mutagenesis of the APX1B Gene

Construction of Recombination Plasmids

Figure 6B:
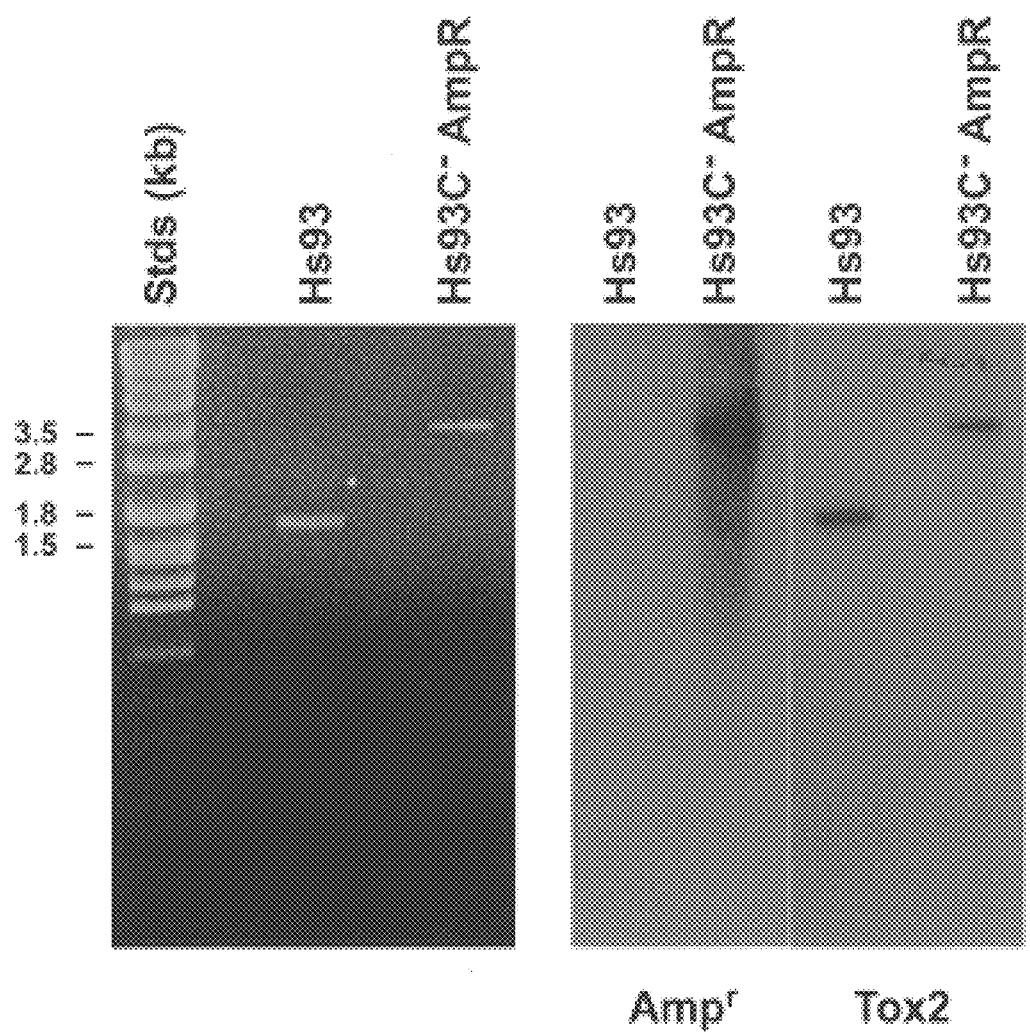
Figure 8A:
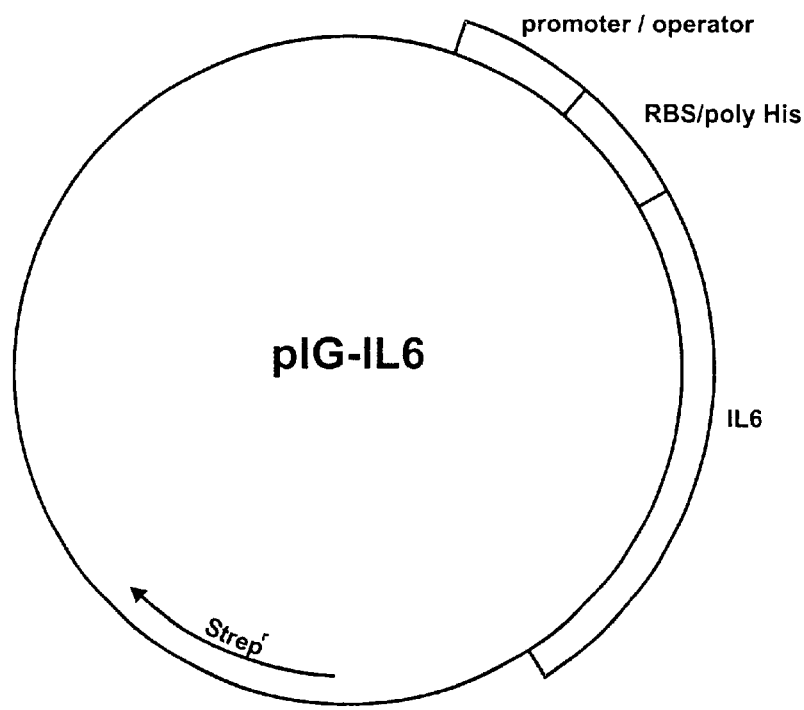
Figure 8B:
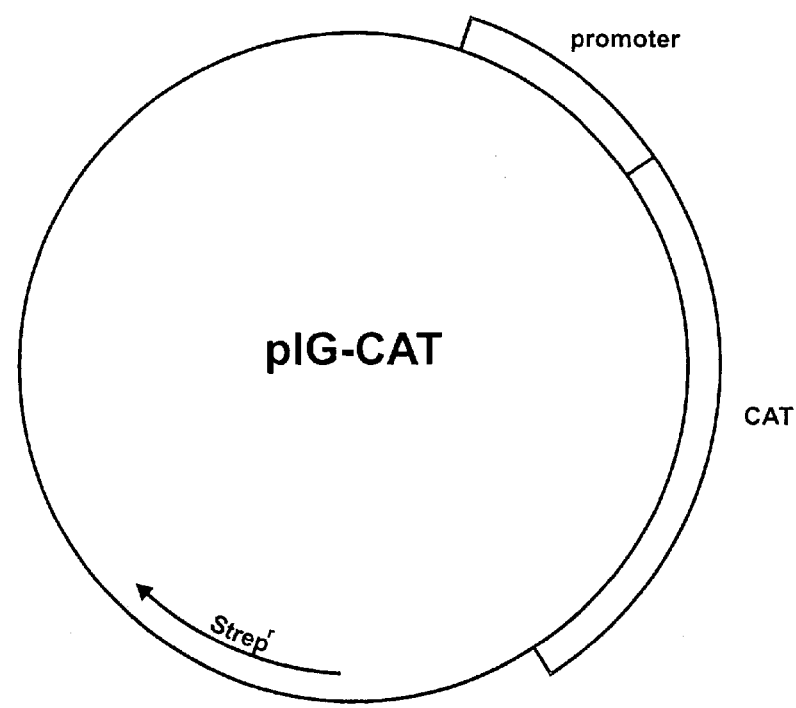
Figure 9:
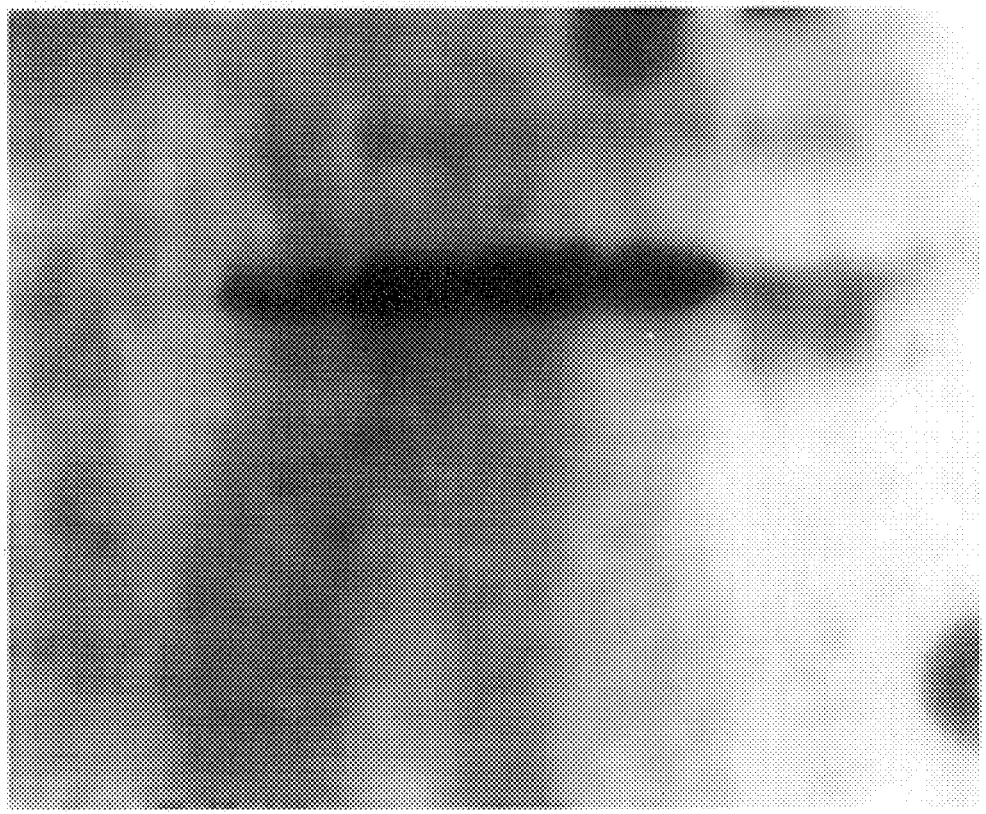

A recombination cassette, designed to allow site specific mutagenesis of the APX1B gene, was constructed by cloning a 2.4 kb EcoRI fragment carrying the APXB (Frey et al., 1993) gene into plC19R (Marsh et al., 1984). A 1.2 kb BamHI fragment carrying the Kanamycin resistance ($Kan^r$) gene from pUC4K (Pharmacia) was cloned into the APX1B gene that had been deleted with BamHI (FIG. 5A). The APX1B gene, with the internal $Kan^r$ gene was isolated as an EcoRI fragment and cloned into the EcoRI site of the APP plasmid vector plG317 (Prideaux et al., 1995) to form the recombination cassette plG3-$BK^r$.

The plasmid plG3-$AMP^r$ was used in plasmid segregation to facilitate the recombination between plG3-$BK^r$ and the APP chromosome. This plasmid was constructed by cloning the Ampercillin resistance gene ($Amp^r$) (Murphy et al) into the multiple cloning site of plG317.

Mutagenesis of the APX1B gene utilised the recombination cassette plG3-$BK^r$, which comprised an EcoRI fragment of the APX1B gene interrupted by a $Kan^r$ gene marker, in the APP plasmid vector plG317 (FIG. 5A). Wild type APP HS22 (Serovarl: APX1 and APX2) was transformed with plG3-$BK^r$ and subsequently with an Ampicillin resistant derivative of plG317 (plG3-$Amp^r$). Cells transformed with both plasmids were selected on media containing both Ampicillin and Kanamycin. To maintain plG3-$Amp^r$, and promote the loss of plG3-$BK^r$ through plasmid segregation, cells containing both plasmids were passaged through media containing only Ampicillin. To identify cells where recombination between plG3-$BK^r$ and the APP chromosome had occurred, cultures were plated onto BHI/AND blood agar plates containing Kanamycin. Any bacterial colony which failed to produce zones of haemolysis on blood agar plates was patched onto a fresh blood agar plate containing Kanamycin. A single colony was identified ($HS22B^-$) that was both Kanamycin resistant and did not produce a zone of haemolysis. This colony was grown in BHI/AND broth containing Kanamycin, and genomic DNA prepared as described previously (Prideaux et al., 1997).

Genomic DNA was isolated from $HS22B^-$, and the host strain HS22 containing plG3-$BK^r$, and examined by PCR using olignucleotides (B5':GCATTTTGGAACAAG; B3': CGGTGATCAAATAGC), SEQ ID NOS:1 and 2 that were designed to anneal to the APP genome outside of the region contained within the recombination cassette (FIG. 5A). Products of the PCR reaction were analysed by Southern blot analysis, as described in materials and methods, using the isolated $Kan^r$ or APX1 B genes as probes (FIG. 6A). From FIG. 6A it can be seen that the region of the APP chromosome containing the APX1B gene, amplified by PCR, is approximately 1.2 kb larger (equivalent to the size of the $Kan^r$ gene) in the non-haemolytic/Kanamycin resistant recombinant $HS22B^-$, than the parent strain HS22. Analysis of the PCR products by Southern-blot confirmed that the products amplified represented the region of the APP chromosome containing the APX1B gene, and in the case of $HS22B^-$ this enlarged region, also hybridised specifically to the Kanr gene. These results confirm that homologous recombination has occurred between the APP chromosome and plG3-$BK^r$ resulting in the site specific transfer of the $Kan^r$ gene onto the APP chromosome.

EXAMPLE 10

Mutagenesis of the APX2C Gene

The plasmid pEP-$C^-Amp^r$ (FIG. 5B) was constructed for use in site specific mutagenesis of the APP APX2C gene. A 3.4 kb fragment containing the APX2C gene, the first 700 bp of the APX2A gene, as well as the region immediately 5' of the APX2 operon was isolated using the PCR, and oligos synthesised using a Pharmacia Gene Assembler Plus DNA Synthesiser (5'CGCACCATGGTCGGGC, 3'ACGTGATCGACMTC) SEQ ID NOS:3 and 4, based on published sequence (Frey et al., 1991). The PCR fragment was cloned into the Mycobacterium/*E. coli* shuttle vector pEP2

(Radford and Hodgson, 1991). The resulting plasmid, pEP2-CA, contains a unique XbaI restriction site located approximately midway in the APXC open reading frame, into which was inserted the Ampercillin resistance gene, to generate the recombination plasmid pEP-$C^-Amp^r$.

Site specific mutagenesis of the APX2C gene utilised the recombination cassette pEP-$C^-$Ampr (FIG. 5B), this cassette is based on the Corynebacterium-*E. coli* shuttle vector pEP2. A number of attempts within our laboratory have failed to transform APP with pEP2, leading us to the conclusion that APP is a non-permissive host for this plasmid vector, and it is therefore a suitable suicide vector for use in APP. Caesium chloride purified pEP-$C^-Amp^r$ DNA was isolated from *E. coli* and linearised with ClaI. Following digestion, the DNA was purified by pheno/lchloroform extraction and ethanol precipitated. A total of 3 $\mu$g of linerised DNA was electroporated into APP HS93 (Serovar7: APX2) using the protocol described previously by Prideaux et al. (1997), and the products of electroporation plated onto BHI/AND blood agar plates containing Ampicillin at a concentration of 1 $\mu$g/ml. A single colony was isolated that was both Ampicillin resistant, and failed to produce a zone of haemolysis on blood agar plates.

Genomic DNA was extracted from the non-zoning/Ampicillin resistant mutant HS93$C^-A^r$, and the parent strain HS93. The polymerase chain reaction was used to examine the region of the APP chromosome containing the APX2C gene, utilising oligonucleotides that bound to the APX2 operon (5'TACAGMCGTTGGTA, 3'ACGTGATCGACAATC), SEQ ID NOS: 5 and 6, at the locations indicated in FIG. 5B. Products of the PCR reactions were characterised by Southern-blot hybridisation, as described in materials and methods, using the isolated $Amp^r$ or APX2C genes as probes (FIG. 6b). The results presented in FIG. 6B show that the $HS93C^-A^r$ mutant produces a PCR product that is approximately 1.5 kb (the size of the Ampr gene) larger than the parent strain HS93. Products of PCR from both bacteria hybridised to the APX2C gene, but only that of the mutant strain hybridised to the $Amp^r$ gene. These results indicated that homologous recombination has occurred between the APP HS93 chromosome and the suicide plasmid vector pEP-C-$A^r$, resulting in transfer of the $Amp^r$ gene onto the APP chromosome in a site specific manner.

Logarithmic cultures of each of the mutant strains, and their parent strains, were examined by western-blotting using antisera raised in rabbits against the secreted proteins of APP HS25 (i.e. Serovarl: APXI and 2), as described under materials and methods.

EXAMPLE 11

Comparison of Virulence of APP Strains in Mice

Overnight cultures of APP HS93, HS22, and the two mutant strains were grown overnight with vigurous shaking at 37° C. in BHI broth supplimented with AND (IO μg/ml) The following day a 1 in 20 dilution of the cultures was made, and the new cultures incubated until an $OD_{600}$ of 0.8 was reached, at this $OD_{600}$ value the viable count of APP is $1 \times 10^9$ cf.u./ml (data not shown). Various dilutions of the cultures were prepared in BHI broth and 200 μl administered IP to 6 week old mice. Mice were observed for the following 24 hrs, after which the percentage of deaths recorded. Under our conditions no mice succumbed to APP infection after this period, the results obtained are presented in Table 5.

TABLE 5

Virulence of APP Parent and Mutant Strains in Mice

| Challenge level ($\times 10^6$) | PERCENT OF DEATHS | | | | |
|---|---|---|---|---|---|
| | HS22 | HS93 | Tox⁻ | H593 C⁻/Amp$^r$ | HS22 B⁻/Kan$^r$ |
| 200 | | 100 | 0 | 0 | 0 |
| 40 | 100 | | | | |
| 20 | | 15 | | | |
| 10 | 100 | 0 | | | |
| 4 | 100 | | | | |

Mice were inoculated intraperitoneally with various levels of APP parent, and mutant strains. Mice that did not succumb to infection within 24 hours were considered to have received a sublethal dose. Results are recorded as the percentage of the population that did not succumb to infection.

EXAMPLE 12

Protection of Pigs Against Heterologous Challenge with APP

Six week old pigs were pre-bled to screen for existing antibodies against APP HS93 (Seroval 7) and APX 2 before animals were incorporated into experimental groups. Nine 6 week old pigs received $1 \times 10^9$ c.f.u. of APP $HS93C^-A^r$, in 1 ml of growth medium, via intra-nasal aerosol inoculation on Day 0. The vaccine was prepared by inoculating 10 ml of BHI/AND (10 μg/ml) with a single colony of $HS93C^-A^r$ and growing with vigorous shaking at 37° C. until an $OD_{600}$ 0.8 was reached. The vaccination schedule was repeated on day 14 as for day 0.

On day 28 pigs were resorted into groups (as outlined below) and either challenged with $2 \times 10^9$ APP HS25 (Serovar 1), in 2 ml of growth media, via the intranasal route, or given 2 ml of BHI broth in a similar manner. The challenge strain was prepared by inoculating a single colony of HS25 into BHI/AND (10 μg/ml) broth and growing until an $OD_{600}$ of 0.8 was reached. At which time the viable count was $1 \times 10^9$ c.f.u./ml.

Numbers of pigs in each group and vaccination/challenge profile were:

| | |
|---|---|
| Group 1 | |
| Unvaccinated and unchallenged | 3 pigs |
| Group 2 | |
| Vaccinated and unchallenged | 3 pigs |
| Group 3 | |
| Unvaccinated and challenged | 6 pigs |
| Group 4 | |
| Vaccinated and challenged | 6 pigs |

The number and severity of lung lesions present in each group upon autopsy, 5 days post challenge, are presented in Table 6. These results clearly demonstrate that vaccination with $HS93C^-A^r$ protected pigs from challenge with the heterologous strain of APP, HS25. The three pigs that were neither vaccinated nor challenged had no detectable lung lesions present at autopsy, indicating that lung lesions present, in other groups of pigs, at the time of autopsy resulted from their treatment post commencement of the vaccine trial. The three pigs that were vaccinated and not challenged also showed no lesions upon autopsy, indicating that the vaccine strain does not induce lung lesions in pigs, that are evident at 2 weeks post-inoculation. Previously we have administered toxin deficient strains of APP to pigs, at similar doses to that of the challenged used in this experiment, and autopsied pigs at day 5 and observed no lesions. The six unvaccinated pigs that were challenged with HS25, all showed numerous lung lesions upon autopsy, indicating that the challenge level used in this experiment was sufficient to induce lesions in unprotected animals. In contrast to the six unvaccinated controls, of the six pigs that had been vaccinated with $HS93C^-A^r$ prior to challenge, only one had any sign of lesions upon autopsy. This was in the form of a single adhesion, in one pig, between the lung and the rib cage, upon closer examination this adhesion appeared to be older than the five days since challenge. Bacteria was isolated from this adhesion and found not to be APP (i.e. did not require AND for growth). Regardless of whether this lesion originated from challenge with APP HS25, this result clearly demonstrates the potential of $HS93C^-A^r$ to protect pigs against an heterologous challenge of virulent APP.

DISCUSSION

The APP serovar 7 strain HS93 was modified by site-specific mutagenesis to inactivate the APXC; gene, throung insertion of the $Amp^r$ gene, without interrupting the expression of the APX A, B or D genes, producing the vaccine strain $HS93C^-A^r$. Evaluation of the vaccine strain in mice showed it to be of reduced virulence compared to the parent strain HS93 (Table 5). The only true evaluation of a vaccine is its ability to protect against disease in the target species. To demonstrate this we vaccinated pigs with $BS93C^-A^r$ via the intranasal route and administered a cross-serovar challenge. The challenge strain used was HS25, which belongs to serovar 1, and produces both APX 1 and 2. This combination of APX production is known to be associated with the most severe outbreaks of pleuropneumonia. Unvaccinated pigs had numerous signs of APP infection upon autopsy, with both lung adhesions and lesions present (Table 6). In contrast only one of the six vaccinated pigs showed any sign of infection, with a single lung adhesion, which was unlikely to be a result of the challenge. This result clearly demonstrates the suitability of the HS93C$^-$A$^r$ strain to be used as a live vaccine against porcine pleuropneumonia. The ability of the vaccine to be delivered via the intra-nasal route was also demonstrated, together with the ability to protect pigs against a cross-serovar challenge. This is the first report of a live vaccine strain of APP suitable for use in pigs to offer cross-serovar protection.

EXAMPLE 13

Expression of Foreign Proteins from APP Vectors

Figure 4:
FIG. 4. Western-blot analysis of APP recombinants. Samples of the APP Tox⁻ strain with (Tox⁻/317-QET1) and without (HS93Tox⁻) the APXA expression cassette were examined by western-blotting along side the parent strains HS93. The blot was probed with rabbit anti-sera, produced within our laboratory, against the APX toxins. From the figure it can be seen that the Tox⁻ strain does not react with anti-APX sera, whilst both the parent strain, HS93, and the Tox⁻ strain containing the APXA expression cassette produce single polypeptides that react specifically with the sera.
Figure 5A:
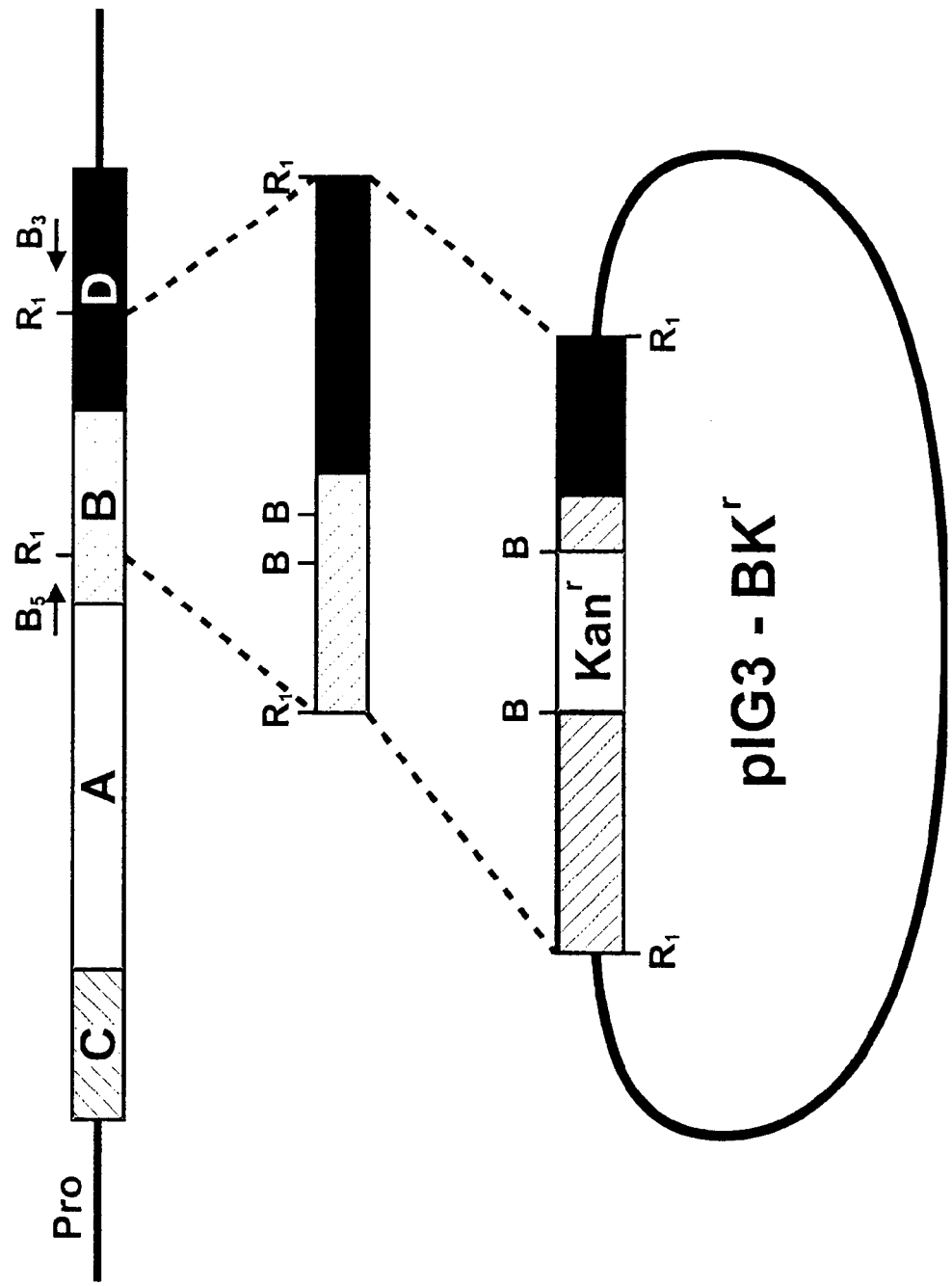
FIG. 5A. The APX1B gene was inactivated on the APP chromosome using the plasmid plG-BK$^r$. An EcoRI restriction fragment, containing a portion of the APX 1B and D genes were isolated from the APP chromosome, and cloned into plC19R. The kanamycin gene was inserted into the BamHI sites of the APX1B gene. The APX1B gene with the internal kanamycin gene was subcloned into plG317 as an EcoRI fragment to form the recombinant cassette plG-3BK$^r$. The binding sites of the oligonucleotides used to characterise the secretion deficient mutant are indicated (B$_5$ and B$_3$). Note both of these oligonucleotides binding outside of the EcoRI fragment used in the recombination cassette.
Figure 5B:
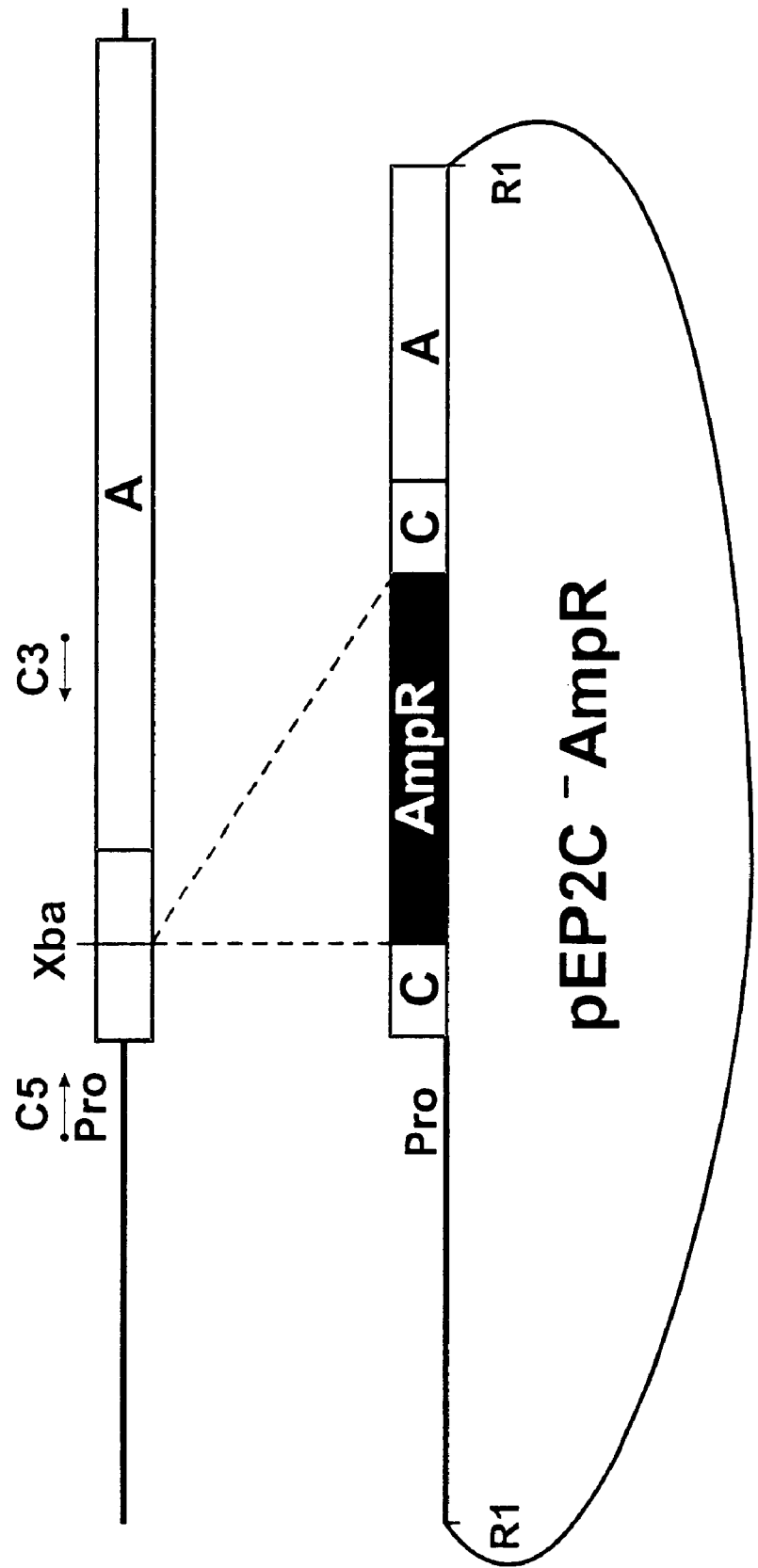
FIG. 5B. The APX2C gene was inactivated on the chromosome using the plasmid vector pEP2C⁻Amp$^r$. A PCR fragment containing the APX2C gene and a portion of the APX2A gene was cloned, and the Amp$^r$ gene inserted into a unique XbaI site within the APX2C gene. The resulting EcoRI fragment was subcloned into pEP2 to form the suicide cassette pEP2C⁻Amp$^r$.

The potential to express foreign genes from APP was demonstrated earlier in this document where the APX1 gene was isolated from a Serovar 1 strain of APP, HS25, and expressed from a plasmid in the modified Serovar 7 strain of APP, HS93 Toxin$^-$. Serovar 7 strains of APP do not encode APX1 genes and the construction of the Tox$^-$/pIG3B-TIK strain, and subsequent evaluation, represents foreign gene expression from APP (FIG. 4). This strain was further characterised and shown to be able to induce anti-APX1 antibodies in mice, in comparison to wild type HS93 or the modified HS93 Toxin$^-$(Table 3). The expression of the APX1 gene from the Tox$^-$strain also produced a live vaccine that was shown to be able to protect mice against an heterologous challenge of APP, once again in contrast to the parent Tox$^-$ strain (Table 4).

To further demonstrate the potential of APP to act as a bacterial vector a series of plG based expression cassettes were constructed for the expression of a number of foreign proteins from APP as outlined in FIG. 8. The genes encoding foreign proteins were cloned along side suitable promoters, in pIG based plasmids, to enable expression in APP. After construction and characterisation in *E. coli* the expression plasmids were transformed into APP as described in materials and methods. Plasmid DNA was isolated from antibiotic resistant colonies and analysed by restriction enzyme digestion to confirm the predicted profiles.

Cytokines are the hormones of the immune system which control and determine the effectiveness of immune responses following infection and vaccination. Cytokines can be used to increase the immune response to a given antigen and to direct the immune response in that direction most appropriate (humoral or cellular) to induce protective immunity. The expression of cytokines from APP vectors may provide a means to optimise the immune response to APP, and any additional, co-expressed, foreign antigens. The porcine IL6 gene was obtained from Dr. David Strom, CSIRO Division of Animal Health, and cloned into a suitable plasmid vector (FIG. 8, plG-IL6) to obtain expression in APP (HS93/plG-IL6). In the case of porcine IL6, expression from APP vectors was detected using a monoclonal antibody (provided by Dr. David Strom, CSIRO Division of Animal Health). From FIG. 9 it can be seen that the monoclonal antibody reacts with a single protein in APP/3B-IL6, of the expected size (22 kDaltons) and identical in size to the *E. coli* derived material. In contrast HS93 without the expression cassette does not react with the monoclonal antibody.

The chloramphenicol acetyl transferase (CAT) gene encoaes an enzyme that offers resistance to the antibiotic chloramphenicol, and is easily quantitated in enzyme reactions. A plasmid was constructed to achieve high level expression of CAT from APP (FIG. 8B), and offered APP strains carrying this plasmid resistance to chloramphenicol.

The development of APP as a bacterial vector will provide a means to deliver commercially significant molecules to the respiratory tract of pigs. These molecules include cytokines, to regulate the immune system, and protective antigens from other pathogenic bacteria, providing the means to construct multi-valent vaccines. Such vaccines have the potential to offer protection against more than one disease following a single vaccination.

Table 6: Lung Lesions Present in Pigs on Autopsy

Pigs were vaccinated twice with APP HS93C$^-$A$^r$ at two week intervals, and then given a cross-serovar challenged with APP HS25, two weeks following the final vaccination. Post mortems were performed five days post-challenge and lung lesions recorded.

Lung Lesions Present In Pigs on Autopsy

Group 1 Unvaccinated and Unchallenged
1. No lesions evident
2. No lesions evident
3. No lesions evident Group 2 Vaccinated and Unchallenged
1 No lesions evident
2. No lesions evident
3. No lesions evident Group 3 Vaccinated and Challenged
1. No lesions evident
2. No lesions evident
3. No lesions evident
4. No lesions evident
5. No lesions evident
6. Small adhesion on left side of lung, appeared to be older than 5 days, walled off (bacteria isolated, found not to be APP)

Group 4 Unvaccinated and Challenged
1. Adhesion right diaphragmatic lobe,
   5 cm diameter lesion left cardiac lobe.
2. 2 adhesions right diaphragmatic lobe,
   Localised lesion (abscess) right diaphragmatic lobe,
   Lesion right ventral diaphragmatic lobe lesion,
   Adhesion left dorsal diaphragmatic lobe,
   2 lesions (0.5cm) dorsal cardiac lobe,
   Lesions mid-ieft diaphragmatic lobe.
3. Small adhesion right posterior apical lobe,
   Pleuritis throughout left dorsal diaphragmatic lobe.
4. Small adhesion right apical lobe,
   Lesion (4 cm) right dorsal diaphragmatic lobe,
   Abscess (1cm) right cardiac lobe,
   Lesions (7×1 cm) throughout left side of lung
5. Exudative pleuritis and inflammation of the pericardium, (diffuse pericarditis)
   Adhesion right diaphragmatic lobe
6. Adhesive pleuritis right diaphragmatic lobe,
   Lesion (1 cm) left ventral diaphragmatic lobe.

Finally, it is to be understood that various alternations, modifications and/or additions may be introduced into the constructions and arrangements of parts previously described without departing from the spirit or ambit of the invention.

REFERENCES

Anderson, C., Potter, A. A., and Gerlach, G.-F. (1991). Isolation and molecular characterization of spontaneously occurring cytolysin-negative mutants of *Actinobacillus pleuropneumoniae* serotype 7. Infect. Immun. 59:4110–4116.

Bhatia, B., Mittal, K. R, and Frey, J. (1991). Factors involved in the immunity against *Actinobacillus plueropneumoniae* in mice. Vet. Microb. 28:147–158.

Coote, J. G. (1992). Structural relationships among the RTX toxin determinants of Gramnegative baceria. FEMS Micro. Rev. 88:137–162.

Fedorka-Cray,P. J., Huether, M. J., Stine, D. L., and Anderson, G. A. (1990). Efficacy of a cell extract from Actinobacillus (Haemophilus) pleuropneumoniae Serotype 1 against disease in swine. Infect. Immun. 58:358–365.

Felmlee, T., Pellet, S., Lee, E. Y., and Welch, R A. (1985). *Escherichia coli* hemolysin is released extracellularly without cleavage of a single peptide. J. Bacte. 163: 88–93.

Fenwick, B. W., and Osburn, B. Y. (1986). Immune responses to the lipopolysaccharides and capsular polysaccharides of *Haemophilus pleuropneumoniae* in convalescent and immunized pigs. Infect. Immun. 54:575–582

Frey, J., and Nicolet, J. (1988). Recognition of hemolysin expression in *Actinobacillus pleuropneumoniae* serotype 1 by Ca2+. Infection and Immunity 26: 2570–2575.

Frey, J., and Nicolet, J. (1990). Hemolysin patterns of *Actinobacillus pleuropneumoniae*. J. Clin. Microbiol. 28: 232–236.

Frey, J., Meier, R, Gygi, D., and Nicolet, J. (1991). Nucleotide sequence ofthe hemolysin I gene from *Actinobacillus pleuropneumoniae*. Infect. Immun. 59: 3026–3032.

Frey, J., van den Bosch, H., Segers, R, and Nicolet, J. (1992). Identification of a second hemolysis (HlyII) in *Actinobacillus pleuropnuemoniae* serotype 1 and expression ofthe gene in *Escherichia coli*. Infect immun. 60: 1671–1676.

Frey, J., Beck, M., Stucki, U., and Nicolet, J. (1993a). Analysis of hemolysin operons in *Actinobacillus pleuropneumoniae*. Gene 123: 51–58.

Frey, J., Bosse, J. T., Chang, Y. -F., Cullen, J. M., Fenwick, B., Gerlach, G. F., Gygi, D., Haesebrouck, F., Inzana, T. J., Jansen, R, Kamp, E. M., Macdonald, J., Macinnes, J. L, Mittal, K. R, Nicolet, J., Rycroft, A. N., Segers, R P. A. M., Smits, M. A., Stenbaek, E., Struck, D. K., van den Bosch, J. F., Willson, P. J., and Young, R. (1993b). *Actinobacillus pleuropneumoniae* RTX-toxins: uniform designation of haemolysins, cytolysins, pleurotoxins and their genes. J. Gen. Micro. 139:1723–1728.

Frey, J., Beck, M., and Nicolet, J. (1994). RTX-toxins of *Actinobacillus pleuropneumoniae*. In Bacterial Protein Toxins. Freer, J., Aitken, R., Alouf, J. E., Boulnois, G., Falmagne, P., Fehrenbach, F., Montecucco, C., Piemont, Y., Rappuoli, R., Wadstrom, T., and Witholt, B. (eds). Stuttgart: Gustav Fischer Verlag, pp. 322–332.

Gerlach, G. -F., Anderson, C., Rossi-Campos, A., and Potter, A. A. (1992). The role ofthe 103 kd *Actinobacillus pleuropeumoniae* cytolysin in virulence and the association of the gene encoding the insertion sequence-like elements. In Proc 12 Int Pig Vet Soc Congr, The Hague, The Netherlands, p 199.

Inzana, T. J., Todd, J., Ma, J., and Veit, H. (1991). Characteriasation of a non-hemolytic mutant of Actinobacillus pleuropneumoniae serotype 5; role of the 110 kilodalton hemolysin in virulence and immunoprotection. Microb. Pathogen 10: 281–296.

Issartel, J. P., Koronakis, V. and Hughes, C. (1991). Activation of *Escherichia coli* prohaemolysin to the mature toxin by acyl carrier protein-dependent fatty acylation. Nature, London, 351:759–761.

Kamp, E. M., Popma, J. K., Anakotta, J., and Smits, M. A. (1991) Identification of hemolytic and cytotoxic proteins of *Actinobacillus pleuropneumoniae* by use of monoclonal antibodies. Infect Immun. 59: 3079–3085.

Kilian, M., and Biberstein, E. L. (1984). Genus II. Haemophilus, p.558–569. In N. R. Krieg and J. G. Holt (ed.), Bergey's manual of systematic bacteriology, vol. 1. The Williams & Wilkins Co., Baltimore.

Komal, J. P. S., and Mittal, K. R. (1990). Grouping of *Actinobacillus pleuropneumoniae* strains of serotypes 1 through 12 on the basis of their virulence in mice. Vet Microbiol. 25: 229–240.

Laemmli, U. K. (1970). Cleavage of structural proteins during the assembly of the head of bacteriophage T4. Nature 227:680–685.

Lenser, D. K., McDonald, T. L., and Miller, N. G. (1988). Protection of mice against lethal effects of an intraperitoneal infection with *Haemophilus* (Actinobacillus) *pleuropneumoniae* after vaccination with capsular proteins. Vet. Microbiol. 18:335–348

Marsh, J. L., Erfle, M., and Wykes, E. J. (1984). The plC plasmid and phage vectors with versatile cloning sites for recombinant selection by insertional activation. Gene 32:482–485.

McKimm-Breschkin, J. L. (1990). The use ofteramethylbenzidine for solid phase immunoassays. J. Immunol. Methods 135:277–280.

Mulks, M., and Thacker, B. (1988). Efficacy of *Haemophilus pleuropneumoniae* outer membrane subunit vaccine in swine. Proc. 10th. Int. Pig Veterinary Society Congress, Rio de Janeiro, Brazil, p.81.

Murphy, G.L. Whitworth L. C. (1994) Construction of isogenic mutants of *Pasteurella haemolytic* by allelic replacement, Gene 148: 101–105.

Pohl, S., Berstchinger, H. U., Frederiksen, W., and Mannheim, W. (1983). Transfer of *Haemophilus pleuropneumoniae* and the *Pasteurella haemolytica*-like organism causing porcine necrotic pleuropneumonia to the genus Actinobacillus (*Actinobacillus pleuropneumoniae* corn. nov.) on the basis of phentoypic and deoxyribonucleic acid relatedness. Int. J. Syst. Bacteriol. 33:510–514.

Radford, A. J., and Hodgson, A. L. M. (1991). Construction and characterisation of a Mycobacterium-*Escherichia coli* shuttle vector. Plasmid 25: 149–153.

Rapp, V. J. and Ross, R F. (1986). Antibody response of swine to outer membrane components of *Haemophilus pleuropneumoniae* during infection. Infect. Immun. 54:751760.

Roendale, S., and Macinnes, J. L (1990). Characterisation of an attenuated strain of Actinobacilluspleuropneumoniae, serotype 1. Am. J. Vet. Res. 51:711–717.

Rosendale, S., Devenish, J., Macinnes, J. I., Lumsden, J. I I., Watson, S. and Xun, H. (1988). Evaluation of heat-sensitive, neutrophil-toxic, and hemolytic activity of *Haemohilus* (Actinobacillus) *pleuorpneumoniae*. American Journal of Veterinary Research 49:1053–1058.

Rycroft, A. N., Williams, D., Cullen, J. M. and Macdonald, J. (1991a). The cytotoxin of *Actinobacillus pleuropneumoniae* (pleurotoxin) is distinct from the haemolysin and is associated with a 120 kDa polypeptide. J. Gen. Microbiol. 137: 561–568.

Rycroft, A. N., Williams, D., McCandlish, I. A. P., and Taylor, D. J. (1991b). Experimental reproduction of acute lesions of porcine pleuropneumonia with a haemolysin-deficientmutant of Actinobacilluspleuropneumoniae. Vet.Rec.16:441–443.

Sambrook, J., Fritsch, E. F., and Maniatis, T. (1989). Molecular cloning: a laboratory manual, 2nd ed. Cold Spring Harbour Laboratory Press, Cold Spring Harbour, N.Y.

Tascon, R T., Rodriguez-Ferri, E. F., Gutierrez-Martin, C. B., Rodriguez-Barbosa, I., Berche, P., and Vazquez-Boland, J. A. (1993). Transposon mutagenesis in *Actinobacillus pleuropneumoniae* with a TnIO derivative. J. Bacteriol. 175: 5717–5722.

Tascnn, R T., Vazquez-Boland, J. A., Gutierrez-Martin, C. B., Rodriguez-Barbosa, I., and Rodriguez-Ferri, E. F. (1994). The RTX haemolysisns ApxI and ApxII are major virulence factors of the swine pathogen *Actinobacillus pleuropneumoniae*: evidence from mutational analysis. Mol. Micro. 14: 207–216.

Udeze, F., A., Latimer, K. S., and Kadis, S. (1987). Role of *Haemophilus pleuropneumoniae* lipopolysaccharide endotoxin in the pathogenesis of porcine *Haemophilus pleuropneumonia*. Am. J. Vet. Res. 48:768–773.

Welch, R A. (1991). Pore-forming cytolysins of Gram-negative bacteria. Mol. Microbiol. 5: 521–528.

Yanisch-Perron, C., Vieira, J., and Messing, J. (1985). Improved M13 phage cloning vectors and host strains: nucleotide sequences ofthe M13mp18 and pUC19 vectors. Gene 33: 103–119.

What is claimed is:

1. A genetically modified strain of *Actinbacillus pleuropneumoniac* (APP) comprising an operon including an RTX A gene and an inactivated RTX C gene and wherein an RTX structural polypeptide is encoded by the RTX A gene and wherein activation of said RTX structural polypeptide is prevented by the inactivated RTX C gene prior to secretion and wherein said RTX structural polypeptide is secreted in a non-toxic form and induces, in a host, protective immunity to the RTX toxin and infection by APP.

2. A modified APP according to claim 1, wherein the RTX C gene is partially or fully deleted.

3. A modified APP according to claim 1, wherein the RTX C gene is inactivated by recombinant DNA techniques including introduction and deletion of DNA from the RTX C gene including single or multiple nucleotide substitution, addition and/or deletion including full or partial deletion of the gene, homologous recombination using a target construct or plasmid segregation; and chemical induced-, radiation induced-, or site specific mutagenesis.

4. The modified APP according to claim 1, wherein the RTX structural polypeptide is an APX selected from the group consisting of APX 1, APX 2, and APX 3.

5. A biological vector consisting essentially of a modified APP according to claim 1.

6. The biological vector according to claim 5, further comprising a gene encoding a biologically active molecule expressed by the biological vector and wherein said molecule is capable of enhancing a response in a host animal.

7. The biological vector according to claim 6, wherein said biological active molecule is selected from the group consisting of functional molecules such as growth factors, hormones, enzymes, antigens and antigenic parts thereof, cytokines such as interleukins, interferons and tumor necrosis factors.

8. The biological vector according to claim 5, wherein said APP is capable of inducing an immune response to two or more antigen epitopes indigenous to APP.

9. The biological vector according to claim 8, wherein said immune response is induced to a virulent form of said APP and to heterologous antigens expressed by said APP.

10. The biological vector according to claim 9, wherein said immune response is induced against an RTX structural polypeptide or RTX toxin and at least one antigen epitope of a pathogenic agent *Pasteurella spp, Haemophilus spp, Serpulina Hyodysenteriae, Lepotsopia spp, Streptocuous spp, E. Coli, Myocobacterium spp*, or viral pathogens including HCV, PRRSV, PRV, TGEV or PPV.

11. A method of producing a recombinantly modified APP which produces an RTX structural polypeptide wherein said RTX structural polypeptide is inactivated, said method comprising providing an APP producing an active RTX structural polypeptide, and an inactivated RTX C gene.

12. The method according to claim 11, wherein the RTX C gene is inactivated by recombinant DNA techniques including introduction and deletion of DNA from the gene encoding the RTX C gene including single or multiple nucleotide substitution, addition and/or deletion including full or partial deletion of the gene homologous recombination using a target construct or plasmid segregation; and chemical induced-, radiation induced-, or site specific mutagenesis.

13. A modified APP prepared according to claim 11.

14. A method for production of an inactive RTX structural polypeptide or toxin, which method comprises culturing a modified APP according to claim 1, and recovering the fully inactive toxin produced by said APP.

15. The biological vector according to claim 8, wherein said immune response is induced against RTX toxin and at least one antigen epitope of a pathogenic agent from *Actinobacillus spp*.

* * * * *

SEQUENCE LISTING

<160> NUMBER OF SEQ ID NOS: 8

<210> SEQ ID NO 1
<211> LENGTH: 15
<212> TYPE: DNA
<213> ORGANISM: Actinobacillus pleuropneumoniae

<400> SEQUENCE: 1
gcattttgga acaag                                                    15

<210> SEQ ID NO 2
<211> LENGTH: 15
<212> TYPE: DNA
<213> ORGANISM: Actinobacillus pleuropneumoniae

<400> SEQUENCE: 2
cggtgatcaa atagc                                                    15

<210> SEQ ID NO 3
<211> LENGTH: 16
<212> TYPE: DNA
<213> ORGANISM: Actinobacillus pleuropneumoniae

<400> SEQUENCE: 3
cgcaccatgg tcgggc                                                   16

<210> SEQ ID NO 4
<211> LENGTH: 15
<212> TYPE: DNA
<213> ORGANISM: Actinobacillus pleuropneumoniae

<400> SEQUENCE: 4
acgtgatcga caatc                                                    15

<210> SEQ ID NO 5
<211> LENGTH: 15
<212> TYPE: DNA
<213> ORGANISM: Actinobacillus pleuropneumoniae

<400> SEQUENCE: 5
tacagaacgt tggta                                                    15

<210> SEQ ID NO 6
<211> LENGTH: 15
<212> TYPE: DNA
<213> ORGANISM: Actinobacillus pleuropneumoniae

```
<400> SEQUENCE: 6
acgtgatcga caatc                                              15

<210> SEQ ID NO 7
<211> LENGTH: 21
<212> TYPE: DNA
<213> ORGANISM: Actinobacillus pleuropneumoniae

<400> SEQUENCE: 7
ggaggatcca tggctaactc t                                       21

<210> SEQ ID NO 8
<211> LENGTH: 26
<212> TYPE: DNA
<213> ORGANISM: Actinobacillus pleuropneumoniae

<400> SEQUENCE: 8
acctacccgg gataggattg ctattt                                  26
```